United States Patent
Nguyen-Kim et al.

(10) Patent No.: US 8,153,740 B2
(45) Date of Patent: Apr. 10, 2012

(54) AMPHOLYTIC COPOLYMER AND USE THEREOF

(75) Inventors: Son Nguyen-Kim, Hemsbach (DE); Horst Schuch, Heidelberg (DE); Thomas Kaiser, Hassloch (DE); Claudia Wood, Weinheim (DE); Peter Hossel, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1516 days.

(21) Appl. No.: 10/541,157

(22) PCT Filed: Dec. 29, 2003

(86) PCT No.: PCT/EP03/14944
§ 371 (c)(1), (2), (4) Date: Jun. 30, 2005

(87) PCT Pub. No.: WO2004/058837
PCT Pub. Date: Jul. 15, 2004

(65) Prior Publication Data
US 2006/0183822 A1     Aug. 17, 2006

(30) Foreign Application Priority Data
Dec. 30, 2002   (DE) ................................. 102 61 750

(51) Int. Cl.
*C08F 126/06*     (2006.01)

(52) U.S. Cl. ........ 526/258; 526/260; 526/264; 526/279; 526/287; 526/288; 526/291; 526/307.4; 526/307.5; 524/555; 524/556; 524/560; 424/70.1; 424/70.11; 424/70.12; 424/70.15; 424/70.16; 424/70.17

(58) Field of Classification Search .................. 524/555, 524/556, 560; 424/70.1, 70.11, 70.12, 70.15, 424/70.16, 70.17; 526/258, 260, 264, 279, 526/287, 288, 291, 307.4, 307.5
See application file for complete search history.

(56) References Cited

U.S. PATENT DOCUMENTS

| | | | |
|---|---|---|---|
| 4,251,651 A | | 2/1981 | Kawakami et al. |
| 5,639,841 A | * | 6/1997 | Jenkins ........................ 526/333 |
| 6,361,768 B1 | * | 3/2002 | Galleguillos et al. ...... 424/70.12 |
| 6,403,074 B1 | * | 6/2002 | Blankenburg et al. ..... 424/70.12 |
| 6,407,158 B1 | | 6/2002 | Kim et al. |
| 6,645,476 B1 | * | 11/2003 | Morschhauser et al. ..... 424/70.1 |
| 2003/0147929 A1 | | 8/2003 | Kim et al. |

FOREIGN PATENT DOCUMENTS

| | | |
|---|---|---|
| EP | 0 100 890 A2 | 2/1984 |
| JP | 2001269197 | 10/2001 |
| WO | WO-00/39176 A1 | 7/2000 |
| WO | 0105365 | 1/2001 |

* cited by examiner

*Primary Examiner* — Bernard Lipman
(74) *Attorney, Agent, or Firm* — Connolly Bove Lodge & Hutz LLP

(57) ABSTRACT

The present invention relates to an ampholytic copolymer, to polyelectrolyte complexes which comprise such an ampholytic copolymer, and to cosmetic or pharmaceutical compositions which comprise at least one ampholytic copolymer or one polyelectrolyte complex.

8 Claims, No Drawings

AMPHOLYTIC COPOLYMER AND USE THEREOF

This application is a National Stage filing of PCT/EP2003/014944 filed Dec. 29, 2003 which in turn claims priority from German Application 102 61 750.3, filed Dec. 30, 2002.

The present invention relates to an ampholytic copolymer, to polyelectrolyte complexes which comprise such an ampholytic copolymer, and to cosmetic or pharmaceutical compositions which comprise at least one ampholytic copolymer or one polyelectrolyte complex.

Polymers with a relatively large number of ionically dissociatable groups in the main chain and/or a side chain are referred to as polyelectrolytes. If these polymers have both anionogenic/anionic and also cationogenic/cationic groups, then they are amphoteric polyelectrolytes or ampholytic polymers. An ionogenic or ionic polymer can react with an oppositely chargeable or charged polymer to form a polyelectrolyte complex (symplex). Ampholytic polymers can in principle form such polyelectrolyte complexes with anionogenic/anionic, cationogenic/cationic and/or at least one further ampholytic polymer. Polyelectrolytes with an adequate number of dissociatable groups are water-soluble or water-dispersible and have found diverse uses in the field of coatings, papermaking auxiliaries, in textile manufacture, and specifically in pharmacy and cosmetics.

Cosmetically and pharmaceutically acceptable water-soluble polymers serve, for example in soaps, creams and lotions, as formulating agents, e.g. as thickener, foam stabilizer or water absorbent or else to alleviate the irritative effect of other ingredients or to improve the dermal application of active ingredients. Their object in hair cosmetics consists in influencing the properties of the hair. In pharmacy, they serve, for example, as coatings or binders for solid medicaments.

For hair cosmetics, film-forming polymers wit ionic groups are used, for example, as conditioner in order to improve the dry and wet combability, the feel to the touch, the shine and the appearance of the hair, and also to impart antistatic properties to the hair. The structure and mode of action of various hair-treatment polymers are described in Cosmetic & Toiletries 103 (1988) 23. Depending on the intended use, water-soluble polymers with cationic functionalities are used which have a high affinity to the negatively charged surface of the hair, which arises due to its structure. Standard commercial cationic conditioner polymers are, for example, cationic hydroxyethylcellulose, cationic polymers based on N-vinylpyrrolidone, e.g. copolymers of N-vinylpyrrolidone and quarternized N-vinyl-imidazole, acrylamide and diallyldimethylammonium chloride. Water-soluble polymers with anionic functionalities, such as, for example, optionally crosslinked polyacrylic acid, serve, for example, as thickener and also carboxylate-group-containing polymers are used, for example, for creating hairstyles.

The provision of products with a complex profile of properties often presents problems. For example, there is a need for polymers for cosmetic compositions which are able to form essentially smooth, tack-free films which impart a pleasant feel to the hair and to the skin and at the same time have a good conditioning action or setting action. Requirements of hair-setting resins are, for example, strong hold at high atmospheric humidity, elasticity, ability to be washed out of the hair, compatibility in the formulation and a pleasant feel of the hair treated therewith. In addition, aesthetic requirements are increasingly placed on cosmetic and pharmaceutical products by the consumer. For example, in the case of such products, a preference for clear, opaque formulations in the form of gels is currently observed. In many cases, the desired profile of properties can only be achieved through the use of two or more polymers with anionic groups. In this connection, however, an incompatibility of the various polymers with one another often arises, which can, for example, lead to undesired salting out. There is therefore a need for cosmetically and pharmaceutically compatible polyelectrolytes which, when used as the sole polymer component, are suitable for providing a certain profile of properties and/or which are compatible with a large number of different polyelectrolytes.

EP-A-0 100 890 describes copolymers obtained by free-radical copolymerization of
a) 20 to 75 parts by weight of at least one $C_2$-$C_{20}$-alkyl ester of (meth)acrylic acid,
b) 5 to 50 parts by weight of at least one nitrogen-containing, neutrally reacting water-soluble monomer,
c) 1 to 25 parts by weight of at least one monomer containing cationic groups and
d) 1 to 25 parts by weight of at least one olefinically unsaturated $C_3$-$C_5$-carboxylic acid which is copolymerizable with a), b) and c).

WO 01/62809 describes a cosmetic composition which comprises at least one water-soluble or water-dispersible polymer, which comprises, in incorporated form,
a) 5 to 50% by weight of at least one $\alpha,\beta$-ethylenically unsaturated monomer with a tert-butyl group,
b) 25 to 90% by weight of at least one N-vinylamide and/or N-vinyllactam,
c) 0.5 to 30% by weight of at least one compound with a free-radically polymerizable, $\alpha,\beta$-ethylenically unsaturated double bond and at least one cationogenic and/or cationic group per molecule, and
d) 0 to 30% by weight of at least one further $\alpha,\beta$-ethylenically unsaturated compound, which may be compounds with at least one anionogenic and/or anionic group per molecule.

EP-A-1038891 describes water-soluble or water-dispersible polymeric salts of at least one polymer and at least one oppositely charged neutralizing agent, where the polymer and the neutralizing agent each has only one type of ionic group.

WO 00/39176 describes a hydrophilic cationic ampholytic copolymer which comprises, in copolymerized form, 0.05 to 20 mol % of an anionic monomer with at least one carboxyl group and 10 to 45 mol % of a cationic monomer with at least one amino group, where the molar ratio of cationic monomer to anionic monomer is about 2:1 to 16:1. These ampholytic copolymers can be used, inter alia, for modifying the rheological properties of bodycare compositions. In the working examples, use is made exclusively of polymers based on methacrylic acid and dimethylaminopropylmethacrylamide, and of acrylic acid and dimethylaminoethyl methacrylate.

It is an object of the present invention to provide novel polyelectrolytes which are suitable for use in cosmetic and pharmaceutical compositions. They should either, when used as the sole polymer component, be suitable for conferring a complex spectrum of requirements and, for example, be able to form tack-free smooth films, have a good setting action and be suitable for the preparation of products in the form of gels, or be compatible with the greatest possible number of different polyelectrolytes for cosmetic and pharmaceutical applications.

We have found that this object is achieved by ampholytic copolymers which comprise, in incorporated form, at least one monomer having at least one anionogenic and/or anionic group per molecule, at least one monomer having at least one cationogenic and/or cationic group per molecule and at least one hydrophilic monomer having an amide group.

The invention therefore provides an ampholytic copolymer obtainable by free-radical copolymerization of
a) at least one compound with a free-radically polymerizable, α,β-ethylenically unsaturated double bond and at least one anionogenic and/or anionic group per molecule,
b) at least one compound with a free-radically polymerizable, α,β-ethylenically unsaturated double bond and at least one cationogenic and/or cationic group per molecule,
c) at least one hydrophilic α,β-ethylenically unsaturated amide-group-containing compound of the formula I

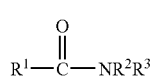
(I)

in which
one of the radicals $R^1$ to $R^3$ is a group of the formula $CH_2=CR^4-$ where $R^4=H$ or $C_1$-$C_4$-alkyl, and the other radicals $R^1$ to $R^3$, independently of one another, are H, alkyl, cycloalkyl, heterocycloalkyl, aryl or hetaryl,
where $R^1$ and $R^2$ together with the amide group to which they are bonded may also be a lactam with 5 to 8 ring atoms,
where $R^2$ and $R^3$ together with the nitrogen atom to which they are bonded may also be a five- to seven-membered heterocycle,
with the proviso that the sum of the carbon atoms of the radicals $R^1$, $R^2$ and $R^3$ is at most 8.

For the purposes of the present invention, the expression alkyl includes straight-chain and branched alkyl groups. Suitable short-chain alkyl groups are, for example, straight-chain or branched $C_1$-$C_7$-alkyl groups, preferably $C_1$-$C_6$-alkyl groups and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

Suitable longer-chain $C_8$-$C_{30}$-alkyl or $C_8$-$C_{30}$-alkenyl groups are straight-chain and branched alkyl or alkenyl groups. Preferably, these are predominantly linear alkyl radicals, as also arise in natural or synthetic fatty acids and fatty alcohols and also oxo alcohols, which may optionally be additionally mono-, di- or polyunsaturated.

These include, for example, n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

Cycloalkyl is preferably $C_5$-$C_8$-cycloalkyl, such as cyclopentyl, cyclohexyl, cycloheptyl or cyclooctyl.

Aryl includes unsubstituted and substituted aryl groups and is preferably phenyl, tolyl, xylyl, mesityl, naphthyl, fluorenyl, anthracenyl, phenanthrenyl, naphthacenyl and in particular is phenyl, tolyl, xylyl or mesityl.

In the text below, compounds which can be derived from acrylic acid and methacrylic acid are sometimes referred to in shortened form by adding the syllable "(meth)" to the compound derived from acrylic acid.

The ampholytic copolymers and polyelectrolyte complexes according to the invention can advantageously be formulated as gels under standard conditions (20° C.). "Gel-like consistency" is shown by compositions which have a higher viscosity than a liquid and which are self-supporting, i.e. they retain the shape given to them without a shape-stabilizing coating. In contrast to solid formulations, however, gel-like formulations can be readily deformed under the application of shear forces. The viscosity of the gel-like compositions is preferably in a range of greater than 600 to about 60 000 mPas. The gels are preferably hair gels which have a viscosity of preferably 6000 to 30 000 mPas.

For the purposes of the present invention, water-soluble monomers and polymers are understood as meaning monomers and polymers which dissolve in an amount of at least 1 g/l at 20° C. in water. Water-dispersible monomers and polymers are understood as meaning monomers and polymers which disintegrate into dispersible particles under the application of shear forces, for example by stirring. Hydrophilic monomers are preferably water-soluble or at least water-dispersible. The copolymers and polyelectrolyte complexes according to the invention are generally water-soluble or at least water-dispersible.

The ampholytic copolymers according to the invention have both anionogenic and/or anionic groups, and also cationogenic and/or cationic groups. For their preparation, preference is given to using monomers with initially uncharged, i.e. with anionogenic and cationogenic groups. In a suitable embodiment these monomers are used together, i.e. in the form of "salt pairs". Preference here is given to using at least some of the compounds a) and b) in the form of a monomer composition, where, for this monomer composition, the molar ratio of anionogenic and anionic groups of component a) to cationogenic and cationic groups of component b) is about 1:1.

If desired, for the preparation of the ampholytic copolymers according to the invention, monomers which are already charged, i.e. monomers with anionic and cationic groups, can also be used instead of uncharged monomers or in addition to uncharged monomers or in addition to salt pairs. The counter ions which carry these monomers are then preferably derived from acids or bases, as are described below for adjusting the pH during the polymerization or of the resulting polymers. Cationic monomers may also be used in partially or completely quaternized form.

Preferably, the quantitative molar ratio of compounds a) to compounds b) (i.e. of anionogenic/anionic compounds to cationogenic/cationic compounds) is in a range from 0.5:1 to less than 2:1 and in particular in a range from 0.7:1 to 1.8:1.

In a suitable embodiment, the ampholytic copolymers according to the invention are outwardly essentially electroneutral. Such copolymers have, bonded to the polymer backbone, anionic and cationic groups in quantitative ratios such that positive and negative charges are essentially balanced. Preferably, the ratio of positive to negative charge equivalents is in a range from 0.8:1 to 1:0.8, particularly preferably 0.9:1 to 1:0.9 and specifically 0.95:1 to 1:0.95.

The pH of a 0.1 molar aqueous solution of the water-soluble ampholytic copolymers according to the invention at a temperature of 20° C. is preferably in a range from 5.5 to 8.0, particularly preferably from 5.6 to 7.5 and in particular from 5.8 to 7.3. Since the ampholytic copolymers according to the invention generally act as buffers, the pH values of their aqueous solutions are generally relatively stable toward dilution and the addition of acids or bases within a wide range.

In the preparation of the ampholytic copolymers according to the invention by free-radical copolymerization in an aqueous medium, the pH is preferably in a range from 5.5 to 9.0, particularly preferably from 5.6 to 8.5 and in particular from 5.8 to 7.5. The pH can be adjusted firstly through appropriate choice of the monomers with anionogenic and cationogenic groups used for the copolymerization. In addition, the pH can be adjusted to the desired value by adding at least one acid or at least one base.

In the preparation of the ampholytic copolymers according to the invention by free-radical copolymerization in nonaqueous media, for example by precipitation polymerization, the monomers are likewise preferably chosen such that the pH of a corresponding aqueous solution is in a range from 5.5 to 8.0, particularly preferably from 5.6 to 7.5 and in particular from 5.8 to 7.3, or an acid or base is added, in order to adjust the pH of a corresponding aqueous solution to a value within this range.

The pH is adjusted by adding at least one suitable acid, e.g. a carboxylic acid, such as lactic acid or tartaric acid, or a mineral acid, such as phosphoric acid, sulfuric acid or hydrochloric acid or by adding at least one suitable base, preferably an alkali metal hydroxide, such as NaOH or KOH, ammonia or an amine, such as triethylamine and in particular an aminoalcohol, such as triethanolamine, methyldiethanolamine, dimethylethanolamine or 2-amino-2-methylpropanol.

The ampholytic copolymer according to the invention preferably comprises, in copolymerized form 0.1 to 25% by weight, particularly preferably 0.5 to 20% by weight, based on the total weight of the components used for the polymerization, of at least one compound a).

The compounds a) are preferably chosen from monoethylenically unsaturated carboxylic acids, sulfonic acids, phosphonic acids and mixtures thereof.

The monomers a) include monoethylenically unsaturated mono- and dicarboxylic acids having 3 to 25, preferably 3 to 6, carbon atoms, which may also be used in the form of their salts or anhydrides. Examples thereof are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. The monomers a) also include the half-esters of monoethylenically unsaturated dicarboxylic acids having 4 to 10, preferably 4 to 6, carbon atoms, e.g. of maleic acid, such as monomethyl maleate. The monomers a) also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrene sulfonic acid, 2-acrylamido-2-methylpropanesulfonic acid, vinylphosphonic acid and allylphosphonic acid. The monomers a) also include the salts of the abovementioned acids, in particular the sodium, potassium and ammonium salts, and also the salts with the abovementioned amines. The monomers a) can be used as such or as mixtures with one another. The proportions by weight given all refer to the acid form.

Component a) is preferably chosen from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof.

Component a) is particularly preferably chosen from acrylic acid, methacrylic acid, itaconic acid and mixtures thereof.

Furthermore, component a) is particularly preferably chosen from 2-acrylamido-2-methyl-1-propanesulfonic acid, styrenesulfonic acid, vinylsulfonic acid, vinyl-phosphonic acid, mixtures thereof and mixtures with the abovementioned monomers a). In particular, use is made of 2-acrylamido-2-methylpropanesulfonic acid as the sole compound of component a), or mixtures which contain 2-acrylamido-2-methylpropanesulfonic acid.

The ampholytic copolymer comprises, in copolymerized form, preferably 0.1 to 40% by weight, particularly preferably 0.5 to 35% by weight, in particular 1 to 30% by weight, based on the total weight of the components used for the polymerization, of at least one compound of component b).

The cationogenic and/or cationic groups of component b) are preferably nitrogen-containing groups, such as primary, secondary and tertiary amino groups, and also quaternary ammonium groups. The nitrogen-containing groups are preferably tertiary amino groups or quaternary ammonium groups. Charged cationic groups can be produced from the amine nitrogens either by protonation, e.g. with monobasic or polybasic carboxylic acids, such as lactic acid, or tartaric acid, or mineral acids, such as phosphoric acid, sulfuric acid and hydrochloric acid, or by quaternization, e.g. with alkylating agents, such as $C_1$-$C_4$-alkyl halides or sulfates. Examples of such alkylating agents are ethyl chloride, ethyl bromide, methyl chloride, methyl bromide, dimethyl sulfate and diethyl sulfate.

Suitable compounds b) are, for example, the esters of α,β-ethylenically unsaturated mono- and dicarboxylic acids with aminoalcohols. Preferred aminoalcohols are $C_2$-$C_{12}$-aminoalcohols which are $C_1$-$C_8$-dialkylated on the amine nitrogen. Suitable as acid component of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof. Preference is given to N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate and N,N-dimethylaminocyclohexyl (meth)acrylate.

Suitable monomers b) are also the amides of the abovementioned α,β-ethylenically unsaturated mono- and dicarboxylic acids with diamines which have at least one primary or secondary amino group. Preference is given to diamines which have a tertiary and a primary or secondary amino group. The monomers b) used are preferably N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide etc. Particular preference is given to using N-[3-(dimethylamino)propyl]acrylamide and/or N-[3-(dimethylamino)propyl]methacrylamide.

Suitable monomers b) are also N,N-diallylamines and N,N-diallyl-N-alkylamines and their acid addition salts and quaternization products. Alkyl is here preferably $C_1$-$C_{24}$-alkyl. Preference is given to N,N-diallyl-N-methylamine and N,N-diallyl-N,N-dimethylammonium compounds, such as, for example, the chlorides and bromides.

Suitable monomers b) are also vinyl- and allyl-substituted nitrogen heterocycles, such as N-vinylimidazole, N-vinyl-2-methylimidazole, vinyl- and allyl-substituted heteroaromatic compounds, such as 2- and 4-vinylpyridine, 2- and 4-allylpyridine, and the salts thereof.

Component b) is preferably chosen from N,N-dimethylaminoethyl (meth)acrylate, N,N-dimethylaminopropyl (meth)acrylate, vinylimidazole and mixtures thereof.

Preferred combinations of components a) and b) which can be used, for example, as salt pair for the free-radical copolymerization are (meth)acrylic acid/N,N-dimethylaminopropyl (meth)acrylate and (meth)acrylic acid/vinylimidazole.

Further preferred combinations of components a) and b) are:
2-acrylamido-2-methylpropanesulfonic acid and
at least one monomer chosen from N-[3-dimethylamino)propyl]methacrylamide, vinylimidazole, N-(tert-butyl)aminoethyl (meth)acrylate, N,N-diallylamine, N,N-diallyl-N-methylamine and mixtures thereof.

Further preferred combinations of components a) and b) are:
styrenesulfonic acid and
at least one monomer chosen from N-[3-(dimethylamino)propyl]methacrylamide, vinylimidazole, N-(tert-butyl)aminoethyl (meth)acrylate, N,N-diallylamine, N,N-diallyl-N-methyl-amine and mixtures thereof.

Further preferred combinations of components a) and b) are:
vinylsulfonic acid and
at least one monomer chosen from N-[3-(dimethylamino)propyl]methacrylamide, vinylimidazole, N-(tert-butyl)aminoethyl (meth)acrylate, N,N-diallylamine, N,N-diallyl-N-methylamine and mixtures thereof.

Further preferred combinations of components a) and b) are:
vinylphosphonic acid and
at least one monomer chosen from N-[3-(dimethylamino)propyl]methacrylamide, vinylimidazole, N-(tert-butyl)aminoethyl (meth)acrylate, N,N-diallylamine, N,N-diallyl-N-methylamine and mixtures thereof.

The ampholytic copolymer according to the invention comprises, in copolymerized form, preferably 40 to 99.8% by weight, particularly preferably 45 to 99% by weight, in particular 50 to 98% by weight, based on the total weight of the components used for the polymerization, of at least one compound c).

The compounds of component c) preferably have at most 7 further carbon atoms in addition to the carbonyl carbon atom of the amide group.

Preferably, the compounds of component c) are chosen from primary amides of $\alpha,\beta$-ethylenically unsaturated monocarboxylic acids, N-vinylamides of saturated monocarboxylic acids, N-vinyllactams, N-alkyl- and N,N-dialkylamides of $\alpha,\beta$-ethylenically unsaturated monocarboxylic acids and mixtures thereof.

Suitable N-alkyl- and N,N-dialkylamides of $\alpha,\beta$-ethylenically unsaturated monocarboxylic acids which have at most 8 further carbon atoms in addition to the carbonyl carbon atom of the amide group are, for example, N-methyl(meth)acrylamide, N-ethyl(meth)acrylamide, N-propyl(meth)acrylamide, N-(n-butyl)(meth)acrylamide, N-tert-butyl(meth)acrylamide, N,N-dimethyl(meth)-acrylamide, N,N-diethyl(meth)acrylamide, piperidinyl(meth)acrylamide, morpholinyl(meth)acrylamide and mixtures thereof.

Particularly preferably, the compounds of component c) are chosen from acrylamide, methacrylamide, N-vinylpyrrolidone, N-vinylcaprolactam, N-vinylformamide, N-vinylacetamide and mixtures thereof.

The water-soluble or water-dispersible copolymers according to the invention can, if desired, comprise, in copolymerized form, up to 20% by weight, preferably up to 15% by weight, particularly preferably 0.1 to 10% by weight, of at least one further monomer d). Preferably, these additional monomers are chosen from esters of $\alpha,\beta$-ethylenically unsaturated mono- and dicarboxylic acids with $C_1$-$C_{30}$-alkanols and $C_1$-$C_{30}$-alkanediols, amides of $\alpha,\beta$-ethylenically unsaturated mono- and dicarboxylic acids with $C_2$-$C_{30}$-aminoalcohols which have a primary or secondary amino group, N-alkyl- and N,N-dialkylamide of $\alpha,\beta$-ethylenically unsaturated monocarboxylic acids which, in addition to the carbonyl carbon atom of the amide group, have more than 8 further carbon atoms, esters of vinyl alcohol and allyl alcohol with $C_1$-$C_{30}$-monocarboxylic acids, vinyl ethers, vinylaromatics, vinyl halides, vinylidene halides, $C_1$-$C_8$-monoolefins, non-aromatic hydrocarbons with at least two conjugated double bonds, siloxane macromers and mixtures thereof.

Preferred monomers d) are esters of $\alpha,\beta$-ethylenically unsaturated mono- and dicarboxylic acids with $C_8$-$C_{30}$-alkanoles and $C_8$-$C_{30}$-alkanediols, particularly preferably with $C_{12}$-$C_{22}$-alkanoles and $C_{12}$-$C_{22}$-alkanedioles.

Preferably monomer d) is chosen from methyl (meth)acrylate, methyl ethacrylate, ethyl (meth)acrylate, ethyl ethacrylate, tert-butyl ethacrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, linolyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate, tert-butyl(meth)acrylamide, n-octyl(meth)acrylamide, 1,1,3,3-tetramethylbutyl (meth)acrylamide, ethylhexyl-(meth)acrylamide, n-nonyl (meth)acrylamide, n-decyl(meth)acrylamide, n-undecyl (meth)acrylamide, tridecyl(meth)acrylamide, myristyl (meth)acrylamide, pentadecyl(meth)acrylamide, palmityl (meth)acrylamide, heptadecyl-(meth)acrylamide, nonadecyl (meth)acrylamide, arrachinyl(meth)acrylamide, behenyl (meth)acrylamide, lignocerenyl(meth)acrylamide, cerotinyl (meth)acryl-amide, melissinyl(meth)acrylamide, palmitoleinyl(meth)acrylamide, oleyl(meth)acrylamide, linolyl(meth)acrylamide, linolenyl(meth)acrylamide, stearyl (meth)acrylamide, lauryl(meth)acrylamide and mixtures thereof. Particular preference is given to the esters of $\alpha,\beta$-ethylenically unsaturated mono- and dicarboxylic acids with linear $C_1$-$C_{30}$-alkanols.

Preferred monomers d) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate etc.

The ampholytic copolymers according to the invention can additionally comprise, in copolymerized form, a surface-active monomer e) different from the components a) to d) and copolymerizable therewith.

Suitable monomers e) are polyether acylates, which, for the purposes of this invention, are generally understood as meaning esters of $\alpha,\beta$-ethylenically unsaturated mono- and dicarboxylic acids with polyetherols. Suitable polyetherols are linear or branched substances which have terminal hydroxyl groups and contain ether bonds. Generally, they have a molecular weight in the range from about 150 to 20 000. Suitable polyetherols are polyalkylene glycols, such as polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers can contain the copolymerized alkylene oxide units in random distribution or in the form of blocks. Preference is given to ethylene oxide/propylene oxide copolymers.

As component e), preference is given to polyether acrylates of the formula II

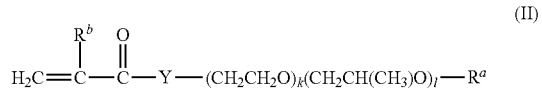

in which
the order of the alkylene oxide units is arbitrary,
k and l, independently of one another, are an integer from 0 to 1000, where the sum of k and l is at least 5,
$R^a$ is hydrogen, $C_1$-$C_{30}$-alkyl or $C_5$-$C_8$-cycloalkyl,
$R^b$ is hydrogen or $C_1$-$C_8$-alkyl,
Y is O or $NR^b$, where $R^b$ is hydrogen, $C_1$-$C_{30}$-alkyl or $C_5$-$C_8$-cycloalkyl.

Preferably, k is an integer from 1 to 500, in particular 3 to 250. l is preferably an integer from 0 to 100.

$R^b$ is preferably hydrogen, methyl, ethyl, n-propyl, isopropyl, n-butyl, sec-butyl, tert-butyl, n-pentyl or n-hexyl, in particular hydrogen, methyl or ethyl.

$R^a$ in the formula II is preferably $C_8$-$C_{30}$-alkyl, in particular $C_{12}$-$C_{30}$-alkyl, such as decyl, undecyl, tridecyl, myristyl, pentadecyl, palmityl, lauryl, stearyl, etc.

Y in the formula II is preferably O or NH.

Suitable polyether acrylates e) are, for example, the polycondensation products of the abovementioned α,β-ethylenically unsaturated mono- and/or dicarboxylic acids and acid chlorides, amides and anhydrides thereof with polyetherols. Suitable polyetherols can be prepared easily by reacting ethylene oxide, 1,2-propylene oxide and/or epichlorohydrin with a starter molecule, such as water or a short-chain alcohol $R^a$—OH. The alkylene oxides can be used individually, alternately or as a mixture. Suitable polyether acrylates e) can also be prepared by transesterification of the esters, described above as component d), of α,β-ethylenically unsaturated mono- and dicarboxylic acids with polyetherols. In this process, product mixtures generally result which contain both the esters used as starting materials and also the polyether acrylates formed as a result of transesterification. These mixtures can generally be used for the preparation of the ampholytic copolymers according to the invention without prior separation. The polyether acrylates e) can be used on their own or in mixtures for the preparation of the polymers used according to the invention.

The ampholytic copolymers according to the invention preferably comprise up to 25% by weight, particularly preferably up to 20% by weight, in particular up to 15% by weight, based on the total weight of the monomers used for the polymerization, of at least one monomer e) in copolymerized form. If a monomer e) is used, then it is done so preferably in an amount of at least 0.1% by weight, particularly preferably at least 1% by weight and in particular at least 5% by weight.

The ampholytic copolymers according to the invention can, if desired, comprise, in copolymerized form, at least one crosslinker f), i.e. a compound with two or more than two ethylenically unsaturated double bonds. Preference is given to using crosslinkers f) in an amount from 0.01 to 10% by weight, particularly preferably 0.03 to 3% by weight, in particular 0.1 to 1% by weight, based on the total weight of the components used for the polymerization.

Crosslinking monomers f) which can be used are compounds with at least two ethylenically unsaturated double bonds, such as, for example, esters of ethylenically unsaturated carboxylic acids, such as acrylic acid or methacrylic acid and polyhydric alcohols, ethers of at least dihydric alcohols, such as, for example, vinyl ethers or allyl ethers.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic neopentyl glycol monoester, 2,2-bis(4-hydroxyphenyl)propane, 2,2-bis[4-(2-hydroxypropyl)-phenyl]propane, diethylene glycol, triethylene glycol, tetraethylene glycol, dipropylene glycol, tripropylene glycol, tetrapropylene glycol, 3-thiopentane-1,5-diol, and also polyethylene glycols, polypropylene glycols and polytetrahydrofurans with molecular weights of in each case 200 to 10 000. Apart from the homopolymers of ethylene oxide or propylene oxide, it is also possible to use block copolymers of ethylene oxide or propylene oxide or copolymers which comprise ethylene oxide and propylene oxide groups in incorporated form. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. It is of course also possible to use the polyhydric alcohols following reaction with ethylene oxide or propylene oxide, in the form of the corresponding ethoxylates or propoxylates. The polyhydric alcohols can also firstly be converted into the corresponding glycidyl ethers by reaction with epichlorohydrin.

Further suitable crosslinkers f) are the vinyl esters or the esters of monohydric, unsaturated alcohols with ethylenically unsaturated $C_3$-$C_6$ carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers f) are esters of unsaturated carboxylic acids with the above-described polyhydric alcohols, for example of oleic acid, crotonic acid, cinnamic acid or 10-undecenoic acid.

Also suitable are straight-chain or branched, linear or cyclic aliphatic or aromatic hydrocarbons which have at least two double bonds, which, in the case of the aliphatic hydrocarbons, must not be conjugated, e.g. divinylbenzene, divinyltoluene, 1,7-octadiene, 1,9-decadiene, 4-vinyl-1-cyclohexene, trivinylcyclo-hexane or polybutadienes with molecular weights of from 200 to 20 000.

Also suitable are amides of unsaturated carboxylic acids, such as, for example, acrylic acid and methacrylic acid, itaconic acid, maleic acid, and N-allylamines of at least difunctional amines, such as, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable are triallylamine or corresponding ammonium salts, e.g. triallylmethylammonium chloride or methyl sulfate, as crosslinkers.

It is also possible to use N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Further suitable crosslinkers f) are divinyldioxane, tetraallylsilane or tetravinylsilane.

Particularly preferred crosslinkers are, for example, methylenebisacrylamide, divinylbenzene, triallylamine and triallylammonium salts, divinylimidazole, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and also allyl or vinyl ethers of polyhydric alcohols, for example 1,2-ethanediol, 1,4-butanediol, diethylene glycol, trimethylolpropane, glycerol, pentaerythritol, sorbitan and sugars, such as sucrose, glucose, mannose.

Particularly preferred crosslinkers f) are pentaerythritol triallyl ether, allyl ethers of sugars such as sucrose, glucose, mannose, divinylbenzene, N,N'-methylenebisacrylamide, N,N'-divinylethyleneurea, and (meth)acrylic esters of glycol, butanediol, trimethylolpropane or glycerol or (meth)acrylic esters of glycol reacted with ethylene oxide and/or epichlorohydrin, butanediol, trimethylolpropane or glycerol. Very particular preference is given to N,N'-methylenebisacrylamide, diallyltartardiamide, diallyl phthalate, diallylurea, glycol di(meth)acrylate, allyl (meth)acrylate, and polyallyl ethers.

According to a suitable variant, the copolymerization for the preparation of the ampholytic copolymers according to the invention takes place in the presence of at least one compound of component g) which is chosen from
g1) polyether-containing compounds,
g2) polymers which have at least 50% by weight of repeat units derived from vinyl alcohol,
g3) cellulose, starch and derivatives thereof,
and mixtures thereof.

If the free-radical copolymerization of the components takes place in the presence of at least one compound of component g), ampholytic copolymers with advantageous properties are obtained. This can be attributed, for example, to the effect of component g) as protective colloid or emulsifier. This can, for example, also result from an at least partial grafting onto component g) as graft base. However, mechanisms other than grafting are also conceivable. The copolymers according to the invention very generally include the process products of free-radical-copolymerization, which is understood as meaning, for example, pure graft polymers, mixtures of graft polymers with ungrafted compounds of component g), copolymers of the abovementioned monomers, and any mixtures. Proportions of ungrafted compounds of component g) may be advantageous depending on the intended use of the ampholytic copolymers. Specific compounds g1) can, for example, have an effect as emulsifier or protective colloid.

Preferably, the amount of component g) used is 1 to 25% by weight, particularly preferably 3 to 20% by weight, based on the total weight of the components used for the polymerization.

Suitable polyether-containing compounds g1) are, for example, water-soluble or water-dispersible nonionic polymers which have alkylene oxide repeat units. Preferably, the proportion of alkylene oxide repeat units is at least 30% by weight, based on the total weight of the compound g1). Suitable polyether-containing compounds g1) are, for example, polyalkylene glycols, polyesters based on polyalkylene glycols, polyether-urethanes, and silicone derivatives containing polyalkylene oxide groups.

Polyalkylene glycols suitable as component g1) generally have a number-average molecular weight in the range from about 150 to 100 000, preferably 300 to 50 000, particularly preferably 500 to 40 000. Suitable polyalkylene glycols are, for example, polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers can comprise, in copolymerized form, the alkylene oxide units in random distribution or in the form of blocks. Advantageously, homopolymers of ethylene oxide or copolymers which comprise ethylene oxide are used. Preferably, the proportion of repeat units derived from ethylene oxide is 40 to 99% by weight. For example, copolymers of ethylene oxide and propylene oxide, copolymers of ethylene oxide and butylene oxide, and also copolymers of ethylene oxide, propylene oxide and at least one butylene oxide are suitable. Also suitable as component g1) are the allyl ethers of the abovementioned polyalkylene glycols.

Branched polyether-containing polymers g1) can be prepared by, for example, adding at least one of the abovementioned alkylene oxides onto polyalcohol radicals, e.g. onto pentaerythritol, glycerol or onto sugar alcohols, such as D-sorbitol and D-mannitol, or onto polysaccharides, such as cellulose and starch. The alkylene oxide units can be present in the addition product in random distribution or in the form of blocks.

It is also possible to use polyesters of polyalkylene oxides and aliphatic or aromatic dicarboxylic acids, e.g. oxalic acid, succinic acid, adipic acid and terephthalic acid, as polyether-containing compound g1). Suitable polyesters of polyalkylene oxides with molar masses of from 1500 to 25 000 are described, for example, in EP-A-0 743 962. Furthermore, it is also possible to use polycarbonates from the reaction of polyalkylene oxides with phosgene or with carbonates, such as, for example, diphenyl carbonate, and also polyurethanes from the reaction of polyalkylene oxides with aliphatic and aromatic diisocyanates as compound g1).

According to a preferred embodiment, a component g1) which includes at least one polyether-urethane is used for the preparation of the ampholytic copolymers.

Suitable polyether-urethanes are the condensation products of polyether polyols, such as polyetherdiols, with polyisocyanates, such as diisocyanates. Suitable polyether polyols are the abovementioned polyalkylene glycols which are obtainable, for example, from the polymerization of cyclic ethers, such as tetrahydrofuran, or from the reaction of one or more alkylene oxides with a starter molecule which has two or more active hydrogen atoms.

Suitable polyisocyanates are chosen from compounds with 2 to 5 isocyanate groups, isocyanate prepolymers with an average number of from 2 to 5 isocyanate groups, and mixtures thereof. These include, for example, aliphatic, cycloaliphatic and aromatic di-, tri- and polyisocyanates. Suitable diisocyanates are, for example, tetramethylene diisocyanate, hexamethylene diisocyanate, 2,3,3-trimethylhexamethylene diisocyanate, 1,4-cyclohexylene diisocyanate, isophorone diisocyanate, 1,4-phenylene diisocyanate, 2,4- and 2,6-tolylene diisocyanate and isomer mixtures thereof (e.g. 80% 2,4- and 20% 2,6-isomer), 1,5-naphthylene diisocyanate, 2,4- and 4,4'-diphenylmethane diisocyanate. A suitable triisocyanate is, for example, triphenylmethane 4,4', 4"-triisocyanate. Also suitable are isocyanate prepolymers and polyisocyanates which are obtainable by addition of the abovementioned isocyanates onto polyfunctional hydroxyl or amine group-containing compounds. Also suitable are polyisocyanates which arise as a result of biuret or isocyanurate formation. Preference is given to using hexamethylene diisocyanate, trimerized hexamethylene diisocyanate, isophorone diisocyanate, 2,4-tolylene diisocyanate, 2,6-tolylene diisocyanate, and mixtures thereof.

According to a further preferred embodiment, a component g1) which includes at least one polyalkylene oxide-containing silicone derivative is used for the preparation of the ampholytic copolymers.

Suitable silicone derivatives g1) are the compounds known under the INCI names Dimethicone copolyols or silicone surfactants, such as, for example, the compounds obtainable under the trade names Abil® (T. Goldschmidt), Alkasil® (Rhône-Poulenc), Silicone Polyol Copolymer® (Genesee), Belsil® (Wacker), Silwet® (OSI) or Dow Corning (Dow Corning). These include compounds with the CAS numbers 64365-23-7; 68937-54-2; 68938-54-5; 68937-55-3.

Particularly suitable compounds g1) are those which comprise the following structural elements:

$$R^7\!-\!\!\begin{bmatrix}R^5\\|\\Si\!-\!O\\|\\R^5\end{bmatrix}_{\!x}\!\!\begin{bmatrix}R^5\\|\\Si\!-\!O\\|\\R^5\end{bmatrix}_{\!y}\!\!\begin{bmatrix}R^5\\|\\Si\!-\!R^6\\|\\R^5\end{bmatrix} \quad (1)$$

where:

$R^6 = CH_3$ or 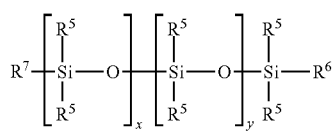

$R^7 = CH_3$ or $R^6$ $\begin{bmatrix}R^5\\|\\Si\!-\!O\\|\\R^5\end{bmatrix}_{\!x}\!\!\begin{bmatrix}R^5\\|\\Si\!-\!CH_3\\|\\R^5\end{bmatrix}$ $R^8 = H, CH_3,$

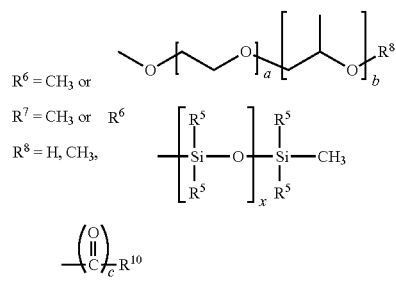

$R^{10}$ is an organic radical of 1 to 40 carbon atoms which can contain amino, carboxylic acid or sulfonate groups or, when c=0 is also the anion of an inorganic acid, and where the radicals $R^5$ may be identical or different, and either originate from the group of aliphatic hydrocarbons having 1 to 20 carbon atoms, are cyclic aliphatic hydrocarbons having 3 to 20 carbon atoms, are of an aromatic nature or

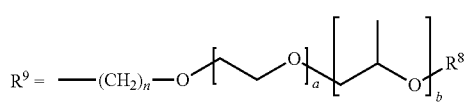

and n is an integer from 1 to 6, x and y are integers such that the molecular weight of the polysiloxane block is between 300 and 30 000, a,b may be integers between 0 and 50, with the proviso that the sum of a and b is greater than 0, and c is 0 or 1.

Preferred radicals $R^6$ and $R^9$ are those in which the sum of a+b is between 5 and 30.

Preferably, the groups $R^5$ are chosen from the following group: methyl, ethyl, propyl, butyl, isobutyl, pentyl, isopentyl, hexyl, octyl, decyl, dodecyl and octadecyl, cycloaliphatic radicals, specifically cyclohexyl, aromatic groups, specifically phenyl or naphthyl, mixed aromatic-aliphatic radicals, such as benzyl or phenylethyl, and also tolyl and xylyl and $R^9$.

Particularly suitable radicals $R^8$ are those in which, when $R^8\!=\!\!-(CO)_c\!-\!R^{10}$, $R^{10}$ is any alkyl, cycloalkyl or aryl radical which has between 1 and 40 carbon atoms and which can carry further ionogenic groups such as $NH_2$, COOH, $SO_3H$.

Preferred inorganic radicals $R^{10}$ are, when c=0, phosphate and sulfate.

Particularly preferred silicone derivatives e) are those of the structure:

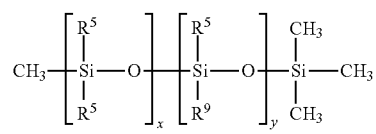

Suitable as graft base are preferably also polymers g2) which have at least 50% by weight of vinyl alcohol units. Preferably, these polymers comprise at least 70% by weight, very particularly preferably 80% by weight, of polyvinyl alcohol units. Such polymers are usually prepared by polymerization of a vinyl ester and subsequent at least partial alcoholysis, aminolysis or hydrolysis. Preference is given to vinyl esters of linear and branched $C_1$-$C_{12}$-carboxylic acids, and very particular preference is given to vinyl acetate. The vinyl esters can of course also be used in a mixture.

Suitable comonomers of the vinyl ester for the synthesis of the graft base g2) are, for example, N-vinylcaprolactam, N-vinylpyrrolidone, N-vinylimidazole, N-vinyl-2-methylimidazole, N-vinyl-4-methylimidazole, 3-methyl-1-vinylimidazolium chloride, 3-methyl-1-vinylimidazolium methyl sulfate, diallylammonium chloride, styrene, alkylstyrenes.

Further suitable comonomers for the preparation of the graft base g2) are, for example, monoethylenically unsaturated $C_3$-$C_6$-carboxylic acids, such as, for example, acrylic acid, methacrylic acid, crotonic acid, fumaric acid, and esters, amides and nitriles thereof, such as, for example, methyl acrylate, ethyl acrylate, methyl methacrylate, ethyl methacrylate, stearyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, maleic anhydride and its half-ester, alkylene glycol (meth)acrylates, acrylamide, methacrylamide, N-dimethylacrylamide, N-tert-butylacrylamide, acrylonitrile, methacrylonitrile, vinyl ethers, such as, for example, methyl, ethyl, butyl or dodecyl vinyl ether, cationic monomers, such as dialkylaminoalkyl (meth)acrylates and dialkylaminoalkyl(meth)acrylamides, such as dimethylaminoethyl acrylate, diethylaminoethyl acrylate, diethylaminoethyl methacrylate, and the salts of the last-mentioned monomers with carboxylic acids or mineral acids, and also the quaternized products.

Preferred graft bases g2) are polymers which are prepared by homopolymerization of vinyl acetate and subsequent at least partial hydrolysis, alcoholysis or aminolysis.

Particularly preferred graft bases g2) are polymers which are prepared by homopolymerization of vinyl acetate and subsequent at least partial saponification. Polymers comprising such polyvinyl alcohol units are obtainable under the name Mowiol®.

As component g), preference is given to using cellulose, cellulose derivatives, starch and/or starch derivatives g3). These include substances which comprise saccharide structures. Such natural substances are, for example, saccharides of vegetable or animal origin or products which are formed by metabolization by microorganisms, and degradation products thereof. Suitable graft bases g3) are, for example, oligosaccharides, polysaccharides, oxidatively, enzymatically or hydrolytically degraded polysaccharides, oxidatively hydrolytically degraded or oxidatively enzymatically degraded polysaccharides, chemically modified oligo- or polysaccharides and mixtures thereof. Preferred products are the compounds specified in U.S. Pat. No. 5,334,287 in column 4, line 20 to column 5, line 45.

Suitable commercially available products are the C-Pur® and C-Dry® products from Cerestar.

If desired, mixtures of compounds of component g) can be used.

A preferred variant are ampholytic copolymers which are obtainable by copolymerization in the presence of at least one compound g1) which is chosen from polyalkylene oxides, polyalkylene oxide-containing silicone derivatives and mixtures thereof.

Preferably, the copolymers according to the invention have a K value (measured in accordance with E. Fikentscher, Cellulose-Chemie 13 (1932), pp. 58-64) on a 1% strength by weight solution in water in the range from about 30 to 300, particularly preferably 40 to 150.

Depending on the K value, the polymers according to the invention are suitable for a large number of cosmetic and pharmaceutical applications. For example, polymers with a K value up to about 50 can advantageously be formulated as sprays (aerosol sprays and pump sprays). Polymers with a K value in a range from about 50 to 90 are advantageously suitable for gels and foams. For shampoos and skin cosmetic applications, polymers with a K value of at least 80 are preferably suitable.

The ampholytic copolymers according to the invention are preferably obtainable by free-radical copolymerization of
  0.1 to 30% by weight, preferably 0.3 to 25% by weight, based on the total weight of the components used for the polymerization, of at least one component a),
  0.1 to 40% by weight, based on the total weight of the components used for the polymerization, of at least one component b),
  40 to 99.8% by weight, based on the total weight of the components used for the polymerization, of at least one component c),
  0 to 20% by weight of at least one further monomer d),
  0 to 10% by weight, preferably 0.1 to 7% by weight, of at least one polyether acrylate e),
  0 to 10% by weight, preferably 0 to 5% by weight, of at least one crosslinker f),
optionally in the presence of up to 25% by weight, based on the total weight of the components used for the polymerization, of at least one component g).

Particular preference is given to ampholytic copolymers obtainable by free-radical copolymerization of
  0.1 to 25% by weight, preferably 0.3 to 20% by weight, based on the total weight of the components used for the polymerization, of at least one monomer which is chosen from acrylic acid, methacrylic acid, 2-acrylamido-2-methylpropanesulfonic acid, styrene-4-sulfonic acid and mixtures thereof,
  1 to 20% by weight, based on the total weight of the components used for the polymerization, of at least one compound b) which is chosen from N,N-dimethylaminopropyl (meth)acrylate, vinylimidazole and mixtures thereof,
  60 to 98.9% by weight, based on the total weight of the components used for the polymerization, of at least one compound c) which is chosen from acrylamide, methacrylamide, N-vinylpyrrolidone, N-vinylcaprolactam, N-vinylformamide and mixtures thereof.

Furthermore, particular preference is given to the ampholytic copolymer obtainable by free-radical polymerization of
  5 to 20% by weight, based on the total weight of the components used for the polymerization, of at least one monomer which is chosen from acrylic acid, methacrylic acid, 2-acrylamido-2-methylpropanesulfonic acid, stryene-4-sulfonic acid and mixtures thereof,
  10 to 30% by weight, based on the total weight of the components used for the polymerization, of at least one compound b) which is chosen from N,N-dimethylaminopropyl (meth)acrylate, vinylimidazole and mixtures thereof,
  50 to 85% by weight, based on the total weight of the components used for the polymerization, of at least one compound c) which is chosen from acrylamide, methacrylamide, N-vinylpyrrolidone, N-vinylcaprolactam, N-vinylformamide and mixtures thereof,
  0 to 25% by weight of at least one further monomer d),
  0 to 10% by weight, preferably 0.1 to 7% by weight, of at least one polyether acrylate e).

The abovementioned particularly preferred copolymers can additionally comprise, in copolymerized form, 0.05 to 1% by weight of at least one crosslinker f). This is, in particular, methyl bisacrylamide and/or N,N'-diallyltartardiamide.

The abovementioned particularly preferred copolymers can additionally comprise, in copolymerized form, 1 to 10% by weight of at least one ester of an α,β-ethylenically unsaturated mono- or dicarboxylic acid with a $C_1$-$C_{30}$-alkanol, preferably stearyl (meth)acrylate.

According to a specific embodiment, the abovementioned particularly preferred copolymers are obtainable by copolymerization in the presence of up to 10% by weight, based on the total weight of the components used for the polymerization, of at least one component g).

A preferred embodiment provides copolymers which consist of repeat units of
  vinylpyrrolidone,
  acrylic acid and/or methacrylic acid,
  dimethylaminoethyl methacrylate or dimethylaminopropylmethacrylamide or vinylimidazole or tert-butylaminoethyl methacrylate and
  at least one polyether acrylate.

A further preferred embodiment provides copolymers which consist of repeat units of
  vinylpyrrolidone,
  2-acrylamido-2-methylpropeanesulfonic acid, dimethylaminoethyl methacrylate or dimethylaminopropylmethacrylamide or vinylimidazole or tert-butylaminoethyl methacrylate and at least one polyether acrylate.

A further preferred embodiment provides copolymers which consist of repeat units of vinylpyrrolidone, acrylamide and/or methacrylamide, acrylic acid and/or methacrylic acid, dimethylaminoethyl methacrylate or dimethylaminopropylmethacrylamide or vinylimidazole or tert-butylaminoethyl methacrylate and at least one polyether acrylate.

A further preferred embodiment provides copolymers which consist of repeat units of vinylpyrrolidone, acrylamide and/or methacrylamide, 2-acrylamido-2-methylpropanesulfonic acid, dimethylaminoethyl methacrylate or dimethylaminopropylmethacrylamide or vinylimidazole or tert-butylaminoethyl methacrylate and at least one polyether acrylate.

A further preferred embodiment provides copolymers which consist of repeat units of vinylpyrrolidone, acrylic acid and/or methacrylic acid, dimethylaminoethyl methacrylate or dimethylaminopropylmethacrylamide or vinylimidazole or tert-butylaminoethyl methacrylate and at least one polyether acrylate, at least one monomer of the formula $$CH_2=CR^c-C(=O)-O-R^d$$

in which $R^c$ is H or methyl and $R^d$ is linear $C_1$-$C_4$-alkyl.

A further preferred embodiment provides copolymers which consist of repeat units of vinylpyrrolidone, 2-acrylamido-2-methylpropanesulfonic acid, dimethylaminoethyl methacrylate or dimethylaminopropylmethacrylamide or vinylimidazole or tert-butylaminoethyl methacrylate and at least one polyether acrylate, at least one monomer of the formula $$CH_2=CR^c-C(=O)-O-R^d$$

in which $R^c$ is H or methyl and $R^d$ is linear $C_1$-$C_4$-alkyl.

A further preferred embodiment provides copolymers which consist of repeat units of vinylpyrrolidone, acrylamide and/or methacrylamide, acrylic acid and/or methacrylic acid, dimethylaminoethyl methacrylate or dimethylaminopropylmethacrylamide or vinylimidazole or tert-butylaminoethyl methacrylate and at least one polyether acrylate, at least one monomer of the formula $$CH_2=CR^c-C(=O)-O-R^d$$

in which $R^c$ is H or methyl and $R^d$ is linear $C_1$-$C_4$-alkyl.

A further preferred embodiment provides copolymers which consist of repeat units of vinylpyrrolidone, acrylamide and/or methacrylamide, 2-acrylamido-2-methylpropanesulfonic acid, dimethylaminoethyl methacrylate or dimethylaminopropylmethacrylamide or vinylimidazole or tert-butylaminoethyl methacrylate and at least one polyether acrylate, at least one monomer of the formula $$CH_2=CR^c-C(=O)-O-R^d$$

in which $R^c$ is H or methyl and $R^d$ is linear $C_1$-$C_4$-alkyl.

The copolymers of the abovementioned preferred embodiments preferably additionally comprise a salt of 2-acrylamido-2-methylpropanesulfonic acid, preferably the sodium salt, in copolymerized form.

The copolymers of the abovementioned preferred embodiments preferably additionally comprise a quaternized monomer containing amine groups, preferably quaternized vinylimidazole, in copolymerized form.

The copolymers of the abovementioned preferred embodiments preferably additionally comprise up to 1% by weight, based on the total weight of the monomers used for the polymerization, of at least one crosslinker in copolymerized form.

The ampholytic copolymers are prepared in accordance with customary processes known to the person skilled in the art, preferably by solution polymerization and precipitation polymerization.

Preferred solvents for solution polymerization are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, polyethylene glycols with number-average molecular weights up to about 3 000, glycerol and dioxane. Particular preference is given to polymerization in water or a water/alcohol mixture, for example a water/ethanol mixture.

The precipitation polymerization takes place, for example, in an ester, such as ethyl acetate or butyl acetate as solvent. The resulting polymer particles precipitate out of the reaction solution and can be isolated by customary methods, such as filtration by means of subatmospheric pressure. In the case of precipitation polymerization, the polymers obtained usually have higher molecular weights than in the case of solution polymerization.

The polymerization temperatures are preferably in a range from about 30 to 120° C., particularly preferably 40 to 100° C. The polymerization usually takes place under atmospheric pressure, although it can also take place under reduced or increased pressure. A suitable pressure range is between 1 and 5 bar.

To prepare the polymers, the monomers, optionally in the presence of component e), can be polymerized using initiators which form free radicals.

Initiators which can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-toloyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane) dihydrochloride or 2-2'-azobis(2-methyl-butyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethane-sulfinate, $H_2O_2/Cu^1$.

To adjust the molecular weight, the polymerization can take place in the presence of at least one regulator. Regulators which can be used are the customary compounds known to the person skilled in the art, such as, for example, sulfur compounds, e.g. mercaptoethanol, 2-ethylhexyl thioglycolate, thioglycolic acid or dodecylmercaptan, and also tribromochloromethane or other compounds which have a regulating effect on the molecular weight of the resulting polymers. A preferred regulator is cysteine.

To achieve the purest possible polymers with a low residual monomer content, the polymerization (main polymerization) can be followed by an afterpolymerization step. The afterpolymerization can take place in the presence of the same initiator system as or a different initiator system to the main polymerization. Preferably, the afterpolymerization takes place at least at the same, preferably at a higher, temperature than the main polymerization. The temperature in the main polymerization and the afterpolymerization is preferably at most 90° C. Preferably, the reaction batch is subjected to a stripping with steam or a steam distillation.

If an organic solvent is used in the preparation of the polymers, then this can be removed by customary processes known to the person skilled in the art, e.g. by distillation at reduced pressure.

As described at the outset, the polymerization preferably takes place at a pH in the range from 5.5 to 8.0, particularly preferably from 5.6 to 7.5 and especially from 5.8 to 7.3. This generally leads to the attainment of the purest possible polymers with a low residual monomer content, which may be attributed to the fact that amines which are formed as cleavage product and which can in some circumstances react with some monomers to give undesired secondary products under the polymerization conditions are removed. The pH is adjusted, as likewise described at the outset, by adding a suitable acid or by adding a suitable base.

Products with particularly high purity and correspondingly advantageous properties for use in cosmetics can be achieved if the reaction product is subjected to a steam distillation or a stripping with steam following the polymerization, optionally before and/or after an afterpolymerization. This treatment with steam also serves, for example, to remove amines and further undesired secondary products which can be removed with steam from the reaction mixture. Preferably, the steam treatment takes place at least between the main polymerization and afterpolymerization. The pH of the polymerization product is preferably adjusted to a value of at most 6.5 prior to the steam treatment. The temperature of the steam used and of the treated polymer solution is preferably at least 90° C.

The polymer solutions can be converted into powder form by various drying processes, such as, for example, spray drying, fluidized spray drying, roller drying or freeze drying. Preference is given to using spray drying. The resulting dry polymer powders can advantageously be converted again into an aqueous solution or dispersion by dissolution or redispersion in water. Pulverulent copolymers have the advantage of better storability, ability to be transported more easily and generally exhibit a lower tendency toward microbial attack.

The anionogenic groups (acid groups) of the polymers can be partially or completely neutralized with a base. The bases used for the neutralization of the polymers may be alkali metal bases, such as sodium hydroxide solution, potassium hydroxide solution, soda, sodium hydrogen carbonate, potassium carbonate or potassium hydrogen carbonate and alkaline earth metal bases, such as calcium hydroxide, calcium oxide, magnesium hydroxide or magnesium carbonate, and also amines. Suitable amines are, for example, $C_1$-$C_6$-alkylamines, preferably n-propylamine and n-butylamine, dialkylamines, preferably diethylpropylamine and dipropylmethylamine, trialkylamines, preferably triethylamine and triisopropylamine. Preference is given to aminoalcohols, e.g. trialkanolamines such as triethanolamine, alkyldialkanolamines, such as methyl- or ethyldiethanolamine, and dialkylalkanolamines, such as dimethylethanolamine, and 2-amino-2-methyl-1-propanol. Particularly for use in hair-treatment compositions, NaOH, KOH, 2-amino-2-methyl-1-propanol, 2-amino-2-ethylpropane-1,3-diol, diethylaminopropylamine and triisopropanolamine have proven successful for the neutralization of the polymers containing acid groups. The neutralization of the acid groups can also be carried out using mixtures of two or more bases, e.g. mixtures of sodium hydroxide solution and triisopropanolamine. The neutralization can take place partially or completely depending on the intended use.

Charged cationic groups can be produced from the present cationogenic nitrogen-containing groups either by protonation, e.g. with mono- or polybasic carboxylic acids, such as lactic acid or tartaric acid, or with mineral acids, such as phosphoric acid, sulfuric acid and hydrochloric acid, or by quaternization, e.g. with alkylating agents, such as $C_1$- to $C_4$-alkyl halides or sulfates. Examples of alkylating agents are ethyl chloride, ethyl bromide, methyl chloride, methyl bromide, dimethyl sulfate and diethyl sulfate.

As a rule, a neutralization takes place such that the pH of a 0.1 molar aqueous solution of the water-soluble ampholytic copolymers according to the invention at a temperature of 20° C. is in a range from 5.5 to 8.0, particularly preferably from 5.6 to 7.5 and in particular from 5.8 to 7.3.

The invention further provides polyelectrolyte complexes which comprise at least one ampholytic copolymer, as defined above, and at least one further poly-electrolyte different therefrom.

Suitable further polyelectrolytes are in principle chosen from polymers with anionogenic and/or anionic groups, polymers which cationogenic and/or cationic groups, ampholytic copolymers and mixtures thereof.

The polyelectrolyte complexes preferably comprise at least one ampholytic copolymer according to the invention and at least one further polyelectrolyte different therefrom in a weight ratio of from about 10:1 to 1:10. Preferably, in the polyelectrolyte complexes according to the invention, the molar ratio of anionogenic and anionic groups to cationogenic and cationic groups is about 0.8:1 to 1:0.8, preferably 0.9:1 to 1:0.9.

Anionic polymers suitable as polyelectrolytes are, for example, homopolymers and copolymers of acrylic acid and methacrylic acid and salts thereof. These also include crosslinked polymers of acrylic acid, as are available under the INCI name Carbomer. Such crosslinked homopolymers of acrylic acid are, for example, commercially available under the name Carbopol® from Noveon (formerly BF GOODRICH). Preference is also given to hydrophobically modified crosslinked polyacrylate polymers, such as Carbopol® Ultrez 21 from Noveon. Polyelectrolyte complexes according to the invention based on homopolymers and copolymers of acrylic acid and methacrylic acid are suitable in advantageous manner for formulation as gels, for example for setting gels, and for the formulation of foams.

Examples of suitable anionic polymers are also acid-modified starches. Acid-modified starches and process for their preparation are known in principle to the person skilled in the art and are described, for example, in Ullmann's Encyclopedia of Industrial Chemistry, 5$^{th}$ edition on CD-ROM, Starch and other Polysaccharides, 1.2.2.1, Wiley-VCH (1997). Polyelectrolyte complexes based on anionically modified starches are suitable in an advantageous manner for formulating gels and for use as conditioner for shampoos.

Further examples of suitable anionic polymers are copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of (meth)acrylic acid and polyether acrylates, where the polyether chain is terminated by a $C_8$-$C_{30}$-alkyl radical. These include, for example, acrylate/beheneth-25-methacrylate copolymers, which are available under the name Aculyn® from Rohm and Haas. Particularly suitable polymers are furthermore copolymers of t-butyl acrylate, ethyl acrylate, methacrylic acid (e.g. Luvimer® 100P), copolymers of ethyl acrylate and methacrylic acid (e.g. Luvimer® MAE and Luviflex® soft), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxyfunctional, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are available commercially, for example, under the names Resyn® (National Starch) and Gafset® (GAF), and vinylpyrrolidone/vinyl acrylate copolymers, obtainable, for example, under the trade name Luviflex® (BASF). Other suitable polymers are the vinylpyrrolidone/acrylate terpolymer available under the name Luviflex® VBM-35 (BASF), and sodium sulfonate-containing polyamides or sodium sulfonate-containing polyesters.

Further suitable polymers are cationic polymers with the INCI name Polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethylsulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), Polymer JR (hydroxyethylcellulose with cationic groups) and vegetable-based cationic polymers, e.g. guar polymers, such as the Jaguar® grades from Rhodia. Also suitable are the polymers with (meth)acrylamide units described in German patent application P 102 43 573.1. In addition, the polymers described in the German patent application P 103 31 870.4, which contain vinylimidazole and/or a derivative thereof in copolymerized form, are also suitable.

Suitable polymers are also amphoteric or zwitterionic polymers, such as the octylacrylamide/methyl methacrylate/tert-butylaminoethyl methacrylate/2-hydroxy-propyl methacrylate copolymers obtainable under the names Amphomer® (National Starch), and zwitterionic polymers as are disclosed for example, in the German patent applications DE 39 29 973, DE 21 50 557, DE 28 17 369 and DE 37 08 451. Acrylamidopropyltrimethylammonium chloride/acrylic acid or methacrylic acid copolymers and the alkali metal and ammonium salts thereof are preferred zwitterionic polymers. Other suitable zwitterionic polymers are methacroylethylbetaine/methacrylate copolymers, which are available commercially under the name Amersette® (AMERCHOL), and copolymers of hydroxyethyl methacrylate, methyl methacrylate, N,N-dimethylaminoethyl methacrylate and acrylic acid (Jordapon®).

The invention further provides a cosmetic or pharmaceutical composition comprising
A) at least one ampholytic copolymer, as defined above, or a polyelectrolyte complex, as defined above, and
B) at least one cosmetically acceptable carrier.

The cosmetically acceptable carrier B) is preferably chosen from
i) water,
ii) water-miscible organic solvents, preferably $C_1$-$C_4$-alkanoles,
iii) oils, fats, waxes,
iv) esters of $C_6$-$C_{30}$-monocarboxylic acids with mono-, di- or trihydric alcohols different from iii),
v) saturated acyclic and cyclic hydrocarbons,
vi) fatty acids,
vii) fatty alcohols
and mixtures thereof.

The compositions according to the invention have, for example, an oil or fatty component B) which is chosen from: hydrocarbons of low polarity, such as mineral oils; linear saturated hydrocarbons, preferably with more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example under the name cyclomethicone.

Preferred oil or fatty components B) are chosen from paraffin and paraffin oils; vaseline; natural fats and oils, such as castor oil, soybean oil, groundnut oil, olive oil, sunflower oil, sesame oil, avocado oil, cocoa butter, almond oil, peach kernel oil, castor oil, cod-liver oil, pork lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti, and mixtures of the abovementioned oil or fatty components.

Suitable cosmetically and pharmaceutically compatible oil or fatty components B) are described in Karl-Heinz Schrader, Grundlagen und Rezepturen der Kosmetika [Fundamentals and Formulations of Cosmetics], 2nd edition, Verlag Hüthig, Heidelberg, pp. 319-355, to which reference is hereby made.

Suitable hydrophilic carriers B) are chosen from water, mono-, di- or polyhydric alcohols having preferably 1 to 8 carbon atoms, such as ethanol, n-propanol, isopropanol, propylene glycol, glycerol, sorbitol, etc.

The cosmetic compositions according to the invention may be skin cosmetic, dermatological or hair cosmetic compositions.

Preferably, the compositions according to the invention are used in the form of a gel, foam, spray, an ointment, cream, emulsion, suspension, lotion, milk or paste. If desired, liposomes or microspheres can also be used.

The cosmetically or pharmaceutically active compositions according to the invention can additionally comprise cosmetically and/or dermatologically active ingredients and auxiliaries.

Preferably, the cosmetic compositions according to the invention comprise at least one ampholytic copolymer as defined above or a polyelectrolyte complex A, at least one carrier B as defined above and at least one constituent different from component A which is chosen from cosmetically active ingredients, emulsifiers, surfactants, preservatives, perfume oils, thickeners, hair polymers, hair and skin conditioners, branched polymers, crosslinked polymers, graft polymers, water-soluble or dispersible silicone-containing polymers, light protection agents, bleaches, gel formers, care agents, colorants, tints, tanning agents, dyes, pigments, bodying agents, moisturizers, refatting agents, collagen, protein hydrolysates, lipids, antioxidants, antifoams, antistats, emollients, softeners.

Suitable cosmetically and/or dermatologically active ingredients are, for example, coloring active ingredients, skin and hair pigmentation agents, tinting agents, tanning agents, bleaches, keratin-hardening substances, antimicrobial active ingredients, light filter active ingredients, repellent active ingredients, substances with hyperemic activity, substances with keratolytic and keratoplastic activity, anti-dandruff active ingredients, antiphlogistics, substances which have a keratinizing effect, substances which act as antioxidants or as free-radical scavengers, skin moisturizers or moisturizers, refatting active ingredients, antierythematous or anti-allergic active ingredients and mixtures thereof.

Artificially skin-tanning active ingredients which are suitable for tanning the skin without natural or artificial irradiation with UV rays are, for example, dihydroxyacetone, alloxan and walnut shell extract. Suitable keratin-hardening substances are usually active ingredients as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus serve both as preservatives and also as a deodorizing substance which reduces the formation or the intensity of body odor. These include, for example, customary preservatives known to the person skilled in the art, such as p-hydroxybenzoates, imidazolidinylurea, formaldehyde, sorbic acid, benzoic acid, salicylic acid, etc. Advantageous preservatives are, for example, paraben esters, such as methylparaben, ethylparaben, propylparaben, etc. A suitable mixture of paraben esters in phenoxyethanol is commercially available under the name Phenonip® (Clairant). Also suitable are chlorinated and nonchlorinated isothiazolones. These are available, for example, under the name Euxyl® K 100 (Schülke & Mayr). Such deodorizing substances are, for example, zinc ricinoleate, triclosan, undecylenic acid alkylolamides, triethyl citrate, chlorhexidine etc. Suitable light filter active ingredients are substances which absorb UV rays in the UV-B and/or UV-A region. Suitable UV filters are, for example, 2,4,6-triaryl-1,3,5-triazines in which the aryl groups may each carry at least one substituent which is preferably chosen from hydroxyl, alkoxy, specifically methoxy, alkoxycarbonyl, specifically methoxycarbonyl and ethoxycarbonyl and mixtures thereof. Also suitable are p-aminobenzoates, cinnamates, benzophenones, camphor derivatives, and pigments which stop UV rays, such as titanium dioxide, talc and zinc oxide. Suitable repellent active ingredients are compounds which are able to drive away or repel certain animals, in particular insects, from humans. These include, for example, 2-ethyl-1, 3-hexanediol, N,N-diethyl-m-toluamide etc. Suitable substances with hyperemic activity which stimulate blood flow through the skin are, for example, ethereal oils, such as dwarf pine, lavender, rosemary, juniper berry, horsechestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, potassium thioglycolate, thioglycolic acid and salts thereof, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics which counter skin irritations are, for example, allantoin, bisabolol, Dragosantol, chamomile extract, panthenol, etc.

The cosmetic compositions according to the invention can comprise, as cosmetic and/or pharmaceutical active ingredient (and also optionally as auxiliary), at least one cosmetically or pharmaceutically acceptable polymer different from compounds of component A). These include very generally polymers which have no anionogenic, anionic, cationogenic or cationic groups on the polymer backbone.

These include neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 37 (BASF); polyamides, e.g. those based on itaconic acid and aliphatic diamines, as are described, for example, in DE-A-43 33 238.

Suitable polymers are also nonionic, siloxane-containing, water-soluble or -dispersible polymers, e.g. polyether siloxanes, such as Tegopren® (Goldschmidt) or Belsil® (Wacker).

The formulation base of pharmaceutical compositions according to the invention preferably comprises pharmaceutically acceptable auxiliaries. Pharmaceutically acceptable auxiliaries are the auxiliaries which are known for use in the fields of pharmacy, food technology and related fields, in particular the auxiliaries listed in the relevant pharmacopoeia (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, antiirritative substances, chelating agents, emulsion stabilizers, film formers, gel formers, odor-masking agents, resins, hydrocolloids, solvents, solubility promoters, neutralizing agents, permeation accelerators, pigments, quaternary ammonium compounds, refatting and superfatting agents, ointment bases, cream bases or oil bases, silicone derivatives, stabilizers, sterilizing agents, propellants, drying agents, opacifiers, thickeners, waxes, softeners, white oils. Formulation in this regard is based on expert knowledge, as given, for example, in Fiedler, H. P. Lexikon der Hilfsstoffe für Pharmazie, Kosmetik und angrenzende Gebiete [Lexicon of auxiliaries for pharmacy, cosmetics and related fields], 4th Ed., Aulendorf: ECV-Editio-Kantor-Verlag, 1996.

To prepare the dermatological compositions according to the invention, the active ingredients can be mixed or diluted with a suitable auxiliary (excipient). Excipients can be solid, semisolid or liquid materials which can serve as vehicle, carrier or medium for the active ingredient. The admixing of further auxiliaries is carried out, where desired, in the manner known to the person skilled in the art.

In a first preferred embodiment, the compositions according to the invention are skin-cleansing compositions.

Preferred skin-cleansing compositions are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations.

According to a further preferred embodiment, the compositions according to the invention are cosmetic compositions for the care and protection of the skin, nail care compositions or preparations for decorative cosmetics.

Particular preference is given to skincare compositions, personal hygiene compositions, foot care compositions, light protection compositions, repellents, shaving compositions, depilatory compositions, antiacne compositions, make-up, mascara, lipsticks, eye shadows, kohl pencils, eyeliners, blushers and eyebrow pencils.

The skincare compositions according to the invention are, in particular, W/O or O/W skin creams, day creams and night creams, eye creams, face creams, antiwrinkle creams, moisturizing creams, bleaching creams, vitamin creams, skin lotions, care lotions and moisturizing lotions.

Skin cosmetic and dermatological compositions based on the abovedescribed polymers or polyelectrolytes A) exhibit advantageous effects. The polymers can, inter alia, contribute to the moisturizing and conditioning of the skin and to an improvement in the feel of the skin. The polymers can also act as thickeners in the formulations. By adding the polymers according to the invention, it is possible to achieve a considerable improvement in skin compatibility in certain formulations.

Skin cosmetic and dermatological compositions preferably comprise at least one ampholytic copolymer or a polyelectrolyte complex A) in an amount of from about 0.001 to 30% by weight, preferably 0.01 to 20% by weight, very particularly preferably 0.1 to 12% by weight, based on the total weight of the composition.

Light protection agents based on component A), in particular, have the property of increasing the residence time of the UV-absorbing ingredients compared with customary auxiliaries such as polyvinylpyrrolidone.

Depending on the field of use, the compositions according to the invention can be applied in a form suitable for skin care, such as, for example, as cream, foam, gel, pencil, mousse, milk, spray (pump spray or spray containing propellant) or lotion.

As well as comprising the ampholytic copolymers or polyelectrolyte complexes A) and suitable carriers, the skin cosmetic preparations can also comprise further active ingredients and auxiliaries customary in skin cosmetics, as described above. These include, preferably, emulsifiers, preservatives, perfume oils, cosmetic active ingredients, such as phytantriol, vitamins A, E and C, retinol, bisabolol, panthenol, light protection agents, bleaches, colorants, tinting agents, tanning agents, collagen, protein hydrolysates, stabilizers, pH regulators, dyes, salts, thickeners, gel formers, bodying agents, silicones, moisturizers, refatting agents and further customary additives.

Preferred oil and fatty components of the skin cosmetic and dermatological compositions are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The polymers according to the invention can also be mixed with traditional polymers where specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkyl siloxanes, polyaryl siloxanes, polyarylalkyl siloxanes, polyether siloxanes or silicone resins.

The cosmetic or dermatological preparations are prepared by customary methods known to the person skilled in the art.

The cosmetic and dermatological compositions are preferably in the form of emulsions, in particular water-in-oil (W/O) emulsions or oil-in-water (O/W) emulsions. It is, however, also possible to choose other types of formulations, for example hydrodispersions, gels, oils, oleogels, multiple emulsions, for example in the form of W/O/W or O/W/O emulsions, anhydrous ointments or ointment bases, etc.

The emulsions are prepared by known methods. Apart from the ampholytic copolymer or polyelectrolyte complex A), the emulsions usually comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The choice of emulsion type-specific additives and the preparation of suitable emulsions is described, for example, in Schrader, Grundlagen und Rezepturen der Kosmetika [Fundamentals and Formulations of Cosmetics], Hüthig Buch Verlag, Heidelberg, 2nd Edition, 1989, third part, to which express reference is made here.

A suitable emulsion, e.g. for a skin cream etc., generally comprises an aqueous phase which is emulsified by means of a suitable emulsifier system in an oil or fatty phase.

The proportion of the emulsifier system in this type of emulsion is preferably about 4 and 35% by weight, based on the total weight of the emulsion. The proportion of the fatty phase is preferably about 20 to 60% by weight. The proportion of the aqueous phase is preferably about 20 and 70%, in each case based on the total weight of the emulsion. The emulsifiers are those customarily used in this type of emulsion. They are chosen, for example, from: $C_{12}$-$C_{18}$-sorbitan fatty acid esters; esters of hydroxystearic acid and $C_{12}$-$C_{30}$-fatty alcohols; mono- and diesters of $C_{12}$-$C_{18}$-fatty acids and glycerol or polyglycerol; condensates of ethylene oxide and propylene glycols; oxypropylenated/oxyethylated $C_{12}$-$C_{18}$-fatty alcohols; polycyclic alcohols, such as sterols; aliphatic alcohols with a high molecular weight, such as lanolin; mixtures of oxypropylenated/polyglycerolated alcohols and magnesium isostearate; succinic esters of polyoxyethylenated or polyoxypropylenated fatty alcohols; and mixtures of magnesium lanolate, calcium lanolate, lithium lanolate, zinc lanolate or aluminum lanolate and hydrogenated lanolin or lanolin alcohol.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is about 250° C. and whose distillation end-point is 410° C., such as, for example, vaseline oil; esters of saturated or unsaturated fatty acids, such as alkyl myristates, e.g. i-propyl, butyl or cetyl myristate, hexadecyl stearate, ethyl or i-propyl palmitate, octanoic or decanoic acid triglycerides and cetyl ricinoleate.

The fatty phase may also comprise silicone oils soluble in other oils, such as dimethylpolysiloxane, methylphenylpolysiloxane and the silicone glycol copolymer, fatty acids and fatty alcohols.

In order to favor the retention of oils, in addition to the ampholytic copolymers or polyelectrolyte complexes A), it is also possible to use waxes, such as, for example, carnauba wax, candililla wax, beeswax, microcrystalline wax, ozokerite wax and the oleates, myristates, linoleates and stearates of Ca, Mg and Al.

The water-in-oil emulsions are generally prepared by introducing the fatty phase and the emulsifier into a reaction vessel. The vessel is heated at a temperature of approximately 50 to 75° C., then the active ingredients and/or auxiliaries which are soluble in oil are added, and water which has been heated beforehand to approximately the same temperature and into which the water-soluble ingredients have optionally been dissolved beforehand is added with stirring. The mixture is stirred until an emulsion of the desired fineness is obtained, which is then left to cool to room temperature, if necessary with a lesser amount of stirring.

According to a further preferred embodiment, the compositions according to the invention are a shower gel, a shampoo formulation or a bath preparation.

Such formulations comprise at least one ampholytic copolymer or one polyelectrolyte complex A) and customary anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickeners/gel formers, skin conditioning agents and moisturizers.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants customarily used in body-cleansing compositions can be used in the washing, shower and bath preparations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The washing, shower and bath preparations can also comprise customary cationic surfactants such as, for example, quaternary ammonium compounds, for example cetyltrimethylammonium chloride.

In addition, it is also possible to use other customary cationic polymers, such as, for example, copolymers of acrylamide and dimethyldiallylammonium chloride (Polyquaternium-7), cationic cellulose derivatives (Polyquaternium-4, -10), guar hydroxypropyltrimethylammonium chloride (INCI: Hydroxylpropyl Guar Hydroxypropyltrimonium Chloride), copolymers of N-vinylpyrrolidone and quaternized N-vinylimidazole (Polyquaternium-16, -44, -46), copolymers of N-vinylpyrrolidone/dimethylaminoethyl methacrylate, quarternized with diethyl sulfate (Polyquaternium-11) and others.

The shower gel/shampoo formulations can further comprise thickeners, such as, for example, sodium chloride, PEG-55, propylene glycol oleate, PEG-120 methyl glucose dioleate and others, and also preservatives, further active ingredients and auxiliaries and water.

In a further preferred embodiment, the compositions according to the invention are hair-treatment compositions.

Hair-treatment compositions according to the invention preferably comprise at least one ampholytic copolymer or a polyelectrolyte complex A) in an amount in the range from about 0.1 to 30% by weight, preferably 0.5 to 20% by weight, based on the total weight of the composition.

The hair-treatment compositions according to the invention are preferably in the form of a setting foam, hair mousse, hair gel, shampoo, hairspray or hair foam.

Hairsprays include both aerosol sprays and also pump sprays without propellant gas. Hair foams include both aerosol foams and also pump foams without propellant gas.

Preferred hair-treatment compositions are in the form of a gel or a foam. Such a hair-treatment composition comprises, for example:
a) 0.1 to 20% by weight, preferably 1 to 10% by weight, of at least one ampholytic copolymer or polyelectrolyte complex A), as defined above,
b) 0.1 to 20% by weight, preferably 1 to 10% by weight, of at least one water-soluble, for example neutral, polymer different from component A)
c) 0 to 40% by weight of at least one carrier (solvent) which is chosen from $C_2$-$C_5$-alcohols, in particular ethanol,
d) 0 to 5% by weight, preferably 0.01 to 5% by weight, particularly preferably 0.2 to 3% by weight, of at least one thickener,
e) 0 to 50% by weight of a propellant,
f) 0 to 10% by weight, preferably 0.1 to 3% by weight, of at least one setting polymer different from a), preferably a water-soluble nonionic polymer,
g) 0 to 1% by weight of at least one refatting agent, preferably chosen from glycerol and glycerol derivatives,
h) 0 to 30% by weight of further active ingredients and/or auxiliaries, e.g. at least one silicone compound,
i) water ad 100% by weight.

The hair-treatment compositions can also be in the form of hairsprays or hair foams. Hairsprays and hair foams preferably comprise predominantly or exclusively water-soluble or water-dispersible components. If the compounds used in the hairsprays and hair foams according to the invention are water-dispersible, they can be used in the form of aqueous microdispersions with particle diameters of, usually, 1 to 350 nm, preferably 1 to 250 nm. The solids contents of these preparations are customarily in a range from about 0.5 to 20% by weight. These microdispersions generally do not require emulsifiers or surfactants for their stabilization.

Preferred hair-treatment compositions are in the form of an aqueous dispersion or in the form of an alcoholic or aqueous-alcoholic solution. Examples of suitable alcohols are ethanol, propanol, isopropanol and mixtures thereof.

Furthermore, the hair-treatment compositions according to the invention can generally comprise customary cosmetic auxiliaries, for example softeners, such as glycerol and glycol; emollients; perfumes; surfactants; UV absorbers; dyes; antistatic agents; agents for improving compatibility; preservatives; and antifoams.

If the compositions according to the invention are formulated as hairspray, they comprise a sufficient amount of a propellant, for example a low-boiling hydrocarbon or ether, such as propane, butane, isobutane or dimethyl ether. Propellants which can be used are also compressed gases, such as nitrogen, air or carbon dioxide. The amount of propellant here can be kept low in order not to increase the VOC content unnecessarily. This is then generally not more than 55% by weight, based on the total weight of the composition. If desired, however, higher VOC contents of 85% by weight and above are also possible.

The ampholytic copolymers according to the invention can also be used in combination with polyelectrolyte complexes according to the invention or in combination with other nonionic hair polymers in the compositions. Suitable polymers are those described above.

The other hair polymers are preferably present in amounts up to 10% by weight, based on the total weight of the composition.

A preferred hair-treatment composition in the form of a hairspray comprises:
a) 0.3 to 20% by weight, preferably 0.5 to 10% by weight, in particular 1 to 5% by weight, of at least one polymer A), as defined above,
b) 50 to 99.5% by weight, preferably 55 to 99% by weight, of a carrier (solvent), chosen from water and water-miscible solvents, preferably $C_2$-$C_5$-alcohols, in particular ethanol, and mixtures thereof,
c) 0 to 50% by weight, preferably 0.1 to 40% by weight, of a propellant, preferably chosen from dimethyl ether and alkanes, such as, for example, propane/butane mixtures,
d) 0 to 10% by weight, preferably 0.1 to 10% by weight, in particular 0.2 to 7% by weight, of at least one hair polymer different from a), preferably a water-soluble or dispersible polymer,
e) 0 to 0.5% by weight, preferably 0.001 to 2% by weight, of at least one water-soluble or water-dispersible silicone compound,
and optionally further active ingredients and/or auxiliaries, as defined above.

The composition according to the invention can comprise, as component e), at least one nonionic, siloxane-containing, water-soluble or -dispersible polymer, in particular chosen from the polyethersiloxanes described above. The proportion of this component is then generally about 0.001 to 2% by weight, based on the total weight of the composition.

The ampholytic copolymers or polyelectrolyte complexes A) are suitable in an advantageous manner as auxiliaries in pharmacy, for the modification of rheological properties (as thickener), as surface-active substance (polymeric emulsifier), preferably as or in (a) coating(s) for the textile, paper, printing and leather industry.

The invention is described in more detail by reference to the nonlimiting examples below.

EXAMPLES

1. Preparation of Copolymers (Solution Polymerization)

Example 14

Copolymer of VP/MAM/DADMAC/DMAPMAM/MAA

| Feed 1: | Monomer mixture of: |
|---|---|
| | 300 g of vinylpyrrolidone |
| | 1200 g of a 15% strength aqueous solution of methacrylamide (=180 g of methacrylamide and 1020 g of water) |
| | 95 g of diallyldimethylammonium chloride |
| | 42 g of dimethylaminopropylmethacrylamide |
| | 21 g of methacrylic acid |
| Feed 2: | Initiator solution of: |
| | 6 g of Wako V 50 [2,2'-azobis(2-amidinopropane) dihydrochloride] and |
| | 123 g of water |
| Feed 3: | Initiator solution of: |
| | 4 g of Wako V 50 [2,2'-azobis(2-amidinopropane) dihydrochloride] and |
| | 82 g of water |

166 g of feed 1, 12.9 g of feed 2 and 137 g of water were initially introduced into a stirred apparatus fitted with reflux condenser, internal thermometer and three separate feed devices, and the mixture was heated to about 65° C. with stirring. Following the start of polymerization, recognizable when the viscosity starts to increase, at 65° C., the remainder of feed 1 was added over the course of 3 h and the remainder of feed 2 over the course of 4 h, during which the internal temperature was increased to about 68° C. When the addition was complete, the reaction mixture was stirred at 70° C. for about a further 2 h. Feed 3 was then added at a temperature of 70° C. over the course of 30 minutes and the polymer solution was then after-polymerized for about a further 2 h at a temperature of about 80° C. The polymer solution was treated with steam for 2 h. This gave an approximately 30% strength polymer solution.

For stabilization, the solution was treated with 100 ppm of Euxyl K100 from Schülke and Mayr (5-chloro-2-methyl-3-(2)-isothiazolone/2-methyl-3-(2H)-isothiazolone/benzyl alcohol).

Pulverulent products were obtained by spray-drying or freeze-drying.

The polymers 1 to 13 were prepared analogously.

2. Preparation of Copolymers (Precipitation Polymerization)

Example 15

Copolymer of VP/VFA/DADMAC/DMAPMAM/MAA/DATDA

| | |
|---|---|
| Feed 1: | Monomer mixture of:<br>240 g of vinylpyrrolidone<br>240 g of vinylformamide<br>105 g of 60% strength diallyldimethylammonium chloride (63 g and 42 g of water)<br>36 g of dimethylaminopropylmethacrylamide<br>18 g of methacrylic acid<br>6 g of 50% strength diallyltartardiamide (3 g and 3 g of water) |
| Feed 2: | Initiator solution of:<br>1.8 g of Wako V 50 [2,2'-azobis(2-amidinopropane) dihydrochloride] and<br>25 g of ethyl acetate |

65 g of feed 1 and 2.7 g of feed 2 in 1370 g of ethyl acetate were initially introduced into a stirred apparatus fitted with reflux condenser, internal thermometer and two separate feed devices and the mixture was heated to about 75° C. with stirring. After the start of polymerization, recognizable from slight clouding, the remainder of feed 1 was added over the course of 3 hours and the remainder of feed 2 over the course of 4 hours, during which the internal temperature was increased to about 78° C. The reaction solution was stirred further under reflux for two hours. The product precipitated out in the form of a fine powder. After cooling, the polymer was filtered off with suction, washed three times with acetone and dried overnight in a drying cabinet at 40° C. under reduced pressure.

The polymers No. 16-30 were prepared analogously.

TABLE 1

| | VP [% by wt.] | Vcap [% by wt.] | MAM [% by wt.] | VFA [% by wt.] | DADMAC [% by wt.] | DMAPMAM:MAA [% by wt.] | VI:AA [% by wt.] | DATDA [% by wt.] | MBAA [% by wt.] |
|---|---|---|---|---|---|---|---|---|---|
| 1 | 70 | 27 | — | — | — | — | 2.5:0.5 | — | — |
| 2 | 70 | — | 26 | — | — | — | 3:1 | — | — |
| 3 | 70 | | — | 26 | — | — | 3:1 | — | — |
| 4 | 60 | 37 | — | — | — | — | 2.5:0.5 | — | — |
| 5 | 60 | — | 37 | — | — | — | 2.5:0.5 | — | — |
| 6 | 60 | | — | 37 | — | — | 2.5:0.5 | — | — |
| 7 | 60 | — | 35.5 | — | — | 3:1.5 | — | — | — |
| 8 | 60 | | — | 35.5 | — | 3:1.5 | — | — | — |
| 9 | 60 | 29.5 | — | — | — | 7:3.5 | — | — | — |
| 10 | 60 | — | 29.5 | — | — | 7:3.5 | — | — | — |
| 11 | 80 | — | — | — | 9.5 | 7:3.5 | — | — | — |
| 12 | 60 | | 20 | — | 9.5 | — | 8:2.5 | — | — |
| 13 | 50 | | 30 | — | 9.5 | 7:3.5 | — | — | — |
| 14 | 40 | — | — | 40 | 9.5 | — | 8:2.5 | — | — |
| 15 | 40 | | — | 40 | 10.5 | 6:3 | — | 0.5 | — |
| 16 | 30 | | — | 30 | 19.5 | 13:7 | — | 0.5 | — |
| 17 | 30 | | — | 30 | 9.5 | 20:10 | — | 0.5 | — |
| 18 | 26 | — | — | 40 | 9.5 | — | 18:6 | — | 0.5 |
| 19 | — | | — | 64.5 | 5 | — | 23:7 | — | 0.5 |
| 20 | — | | — | 64.5 | 5 | 20:10 | — | — | 0.5 |

TABLE 2

| | VP [% by wt.] | Vcap [% by wt.] | SMA [% by wt.] | VFA [% by wt.] | DMAP-MAM:MAA [% by wt.] | MBAA [% by wt.] |
|---|---|---|---|---|---|---|
| 21 | 63.8 | — | — | — | 24:12 | 0.2 |
| 22 | 40 | 23.8 | — | — | 24:12 | 0.2 |
| 23 | 40 | — | — | 23.8 | 24:12 | 0.2 |
| 24 | — | 23.8 | — | 40 | 24:12 | 0.2 |
| 25 | — | — | — | 63.8 | 24:12 | 0.2 |
| 26 | 52 | — | 2.8 | — | 30:15 | 0.2 |
| 27 | 30 | 22 | 2.8 | — | 30:15 | 0.2 |
| 28 | 30 | — | 2.8 | 22 | 30:15 | 0.2 |
| 29 | — | 30 | 2.8 | 22 | 30:15 | 0.2 |
| 30 | — | — | 2.8 | 52 | 30:15 | 0.2 |

VP = vinylpyrrolidone
Vcap = vinylcaprolactam
MAM = methacrylamide
VFA = vinylformamide
DADMAC = diallyldimethylammonium chloride
DMAPMAM = dimethylaminopropylmethacrylamide
MAA = methacrylic acid
VI = vinylimidazole
AA = acrylic acid
DATDA = N,N'-diallyltartardiamide
MBAA = methylbisacrylamide
SMA = stearyl methacrylate 3. Application Examples
   Use in HAIR Cosmetics:
1) Hair gels containing an anionic thickener: example Nos 21-28

| | [%] | CTFA |
|---|---|---|
| Phase 1: | | |
| Polymer 1-8 (30% strength aqueous solution) | 10.0 | |
| Glycerol | 0.3 | |
| Water dist. | 39.2 | |
| Further additives: preservatives, soluble ethoxylated silicone, perfume | q.s. | |
| Phase 2: | | |
| Carbopol 940 (1% strength aqueous suspension) | 30.0 | Carbomer |
| Triethanolamine | 0.5 | |
| Water dist. | 20.0 | |

To prepare hair gels, the components are weighed in and homogenized. Phase 2 forms a clear, solid gel into which phase 1 is slowly stirred.

2) Hair gels containing a further setting polymer and anionic thickener: example Nos 29-36

| | [%] | CTFA |
|---|---|---|
| Phase 1: | | |
| Polymer 1-8 (30% strength aqueous solution) | 7.0 | |
| Luviskol VA 64 | 1.0 | Vinylpyrrolidonevinyl acetate copolymer |
| Belsil DMC 60 31 | 0.1 | ethoxylated polydimethylsiloxane |
| Uvinul MS 40 | 0.2 | Benzophenone-4 |
| Glycerol | 0.1 | |
| D-Panthenol USP | 0.1 | Panthenol |
| Ethanol | 20.0 | |
| Water dist. | 21.0 | |
| Further additives: preservatives, soluble ethoxylated silicone, perfume | q.s. | |
| Phase 2: | | |
| Carbopol 940 (1% strength aqueous suspension) | 30.0 | Carbomer |
| Triethanolamine | 0.5 | |
| Water dist. | 20.0 | |

Preparation: The components of the two phases are homogenized after being weighed in. Phase 2 forms a clear, solid gel. Phase 1 is slowly stirred into phase 2.

3) Liquid Hair Gels: Example Nos 37-50

| | [%] | CTFA |
|---|---|---|
| Polymer 1-14 (30% strength aqueous solution) | 5.3 | |
| Natrosol 250 L (2% strength aqueous solution) | 25.0 | Hydroxyethyl cellulose (Hercules) |
| C-Dry MD 1915 (10% strength aqueous solution) | 25.0 | Degraded starch (Cerestar) |
| Water dist. | 44.7 | |
| Further additives: preservatives, soluble ethoxylated silicone, perfume | q.s. | |

Preparation: Weigh in and slowly homogenize at room temperature.

4) Cationic Self-Thickening Hair Gels (Without Additional Thickener): Example Nos. 51-56

| | [%] | CTFA |
|---|---|---|
| Phase 1: | | |
| Polymer 15-20 (in powder form) | 3.0 | |
| Glycerol | 0.1 | |
| Water dist. | 96.6 | |
| Further additives: preservatives, soluble ethoxylated silicone, perfume | q.s. | |
| Phase 2: | | |
| 45% strength phosphoric acid | | |

Preparation: The components of phase 1 are weighed in, homogenized at 40° C. and then phase 2 is added with stirring until a pH of 5.5 to 6 was reached.

5) Anionic self-thickening hair gels (without additional thickener): example Nos. 57-60

|  | [%] | CTFA |
|---|---|---|
| Phase 1: | | |
| Polymer 17-20 (in powder form) | 3.0 | |
| Glycerol | 0.1 | |
| Water dist. | 96.9 | |
| Further additives: preservatives, soluble ethoxylated silicone, perfume | q.s. | |
| Phase 2: | | |
| Aminomethylpropanol (45% strength aqueous solution) | | |

Preparation: The components of phase 1 were weighed, homogenized at 40° C. and then phase 2 was added with stirring until a pH of 8.5 was reached.

4. Preparation of Copolymers Based on 2-acrylamido-2-methylpropanesulfonic Acid

General preparation procedure: Solution polymerization in ethanol/water (1:1)

Example 60

500 g of a 30% strength polymer solution (AMPS/Na AMPS/DMAPMAM/VP/fatty alcohol ethoxylate MA)

| Feed 1: | Monomer mixture of: |
|---|---|
| 120 g | of vinylpyrrolidone |
| 7.5 g | of $C_{16}/C_{18}$-fatty alcohol ethoxylate methacrylate (25 EO) |
| 7.5 g | of 2-acrylamido-2-methylpropanesulfonic acid (AMPS) |
| 7.5 g | of AMPS sodium salt |
| 7.5 g | of dimethylaminopropylmethacrylamide |
| Feed 2: | Initiator solution of: |
| 0.3 g | of Wako ® 50 [2,2'-azobis(2-amidinopropane) dihydrochloride] |
| 105 g | of water |
| Feed 3: | Initiator solution of: |
| 0.75 g | of tert-butyl perpivalate, 75% strength |
| 61.5 g | of ethanol |
| Feed 4: | |
| 1 g | of NaOH |
| 28 g | of water |

11 g of feed 1, 5 g of feed 2, 70 g of water and 44 g of ethanol were initially introduced into a stirred apparatus fitted with reflux condenser, internal thermometer and four separate feed devices, and the mixture was heated to about 70° C. with stirring. Following the start of polymerization, recognizable from a slight increase in the viscosity, at 70° C., the remainder of feed 1 was added over the course of three hours and the remainder of feed 2 over the course of four hours, during which the internal temperature was increased to about 73° C. The reaction solution was then further stirred for about two hours at 70° C. and then feed 3 was metered in over the course of 30 minutes at 70° C. Following the addition, the mixture was after-polymerized for about a further two hours at a temperature of 80° C. The polymer solution was adjusted to pH 8 with NaOH solution (feed 4, addition time 10 minutes). This gave an approximately 30% strength aqueous/ethanolic solution.

The polymers Nos. 31-59 and 61-80 were prepared analogously.

TABLE 3

| Ex. No. | VP [% by wt.] | MAM [% by wt.] | AMPS [% by wt.] | DMAPMAM [% by wt.] | VI [% by wt.] | NtBAEMA [% by wt.] | FAEMA [% by wt.] | Plex 6877-0 [% by wt.] | MBAA | Neutralized to pH 6-8 with |
|---|---|---|---|---|---|---|---|---|---|---|
| 31 | 98 | — | 0.55 | 0.45 | — | — | 1.0 | — | — | AMP |
| 32 | 97 | — | 0.65 | — | 0.35 | — | 2.0 | — | — | AMP |
| 33 | 97 | — | 0.55 | 0.45 | — | — | 2.0 | — | — | AMP |
| 34 | 96.5 | — | 0.55 | — | — | 0.45 | 2.5 | — | — | AMP |
| 35 | 95 | — | 1.1 | 0.9 | — | — | 3.0 | — | — | AMP |
| 36 | 94 | — | 0.55 | 0.45 | — | — | 5.0 | — | — | AMP |
| 37 | 90 | — | 3.4 | — | 1.6 | — | 5.0 | — | — | AMP |
| 38 | 90 | — | 2.7 | 2.3 | — | — | 5.0 | — | — | AMP |
| 39 | 90 | — | 2.7 | — | — | 2.3 | 5.0 | — | — | AMP |
| 40 | 87 | — | 3.4 | — | 1.6 | — | 8.0 | — | — | AMP |
| 41 | 87 | — | 2.7 | 2.3 | — | — | 8.0 | — | — | AMP |
| 42 | 85 | — | 5.4 | 4.6 | — | — | 5.0 | — | — | NaOH***) |
| 43 | 75 | — | 11 | 9 | — | — | 5.0 | — | — | NaOH***) |
| 44 | 70 | — | 11 | 9 | — | — | 10.0 | — | — | NaOH***) |
| 45 | 55 | — | 22 | 18 | — | — | 5.0 | — | — | NaOH***) |
| 46 | 77 | 20 | 0.55 | 0.45 | — | — | 2.0 | — | — | AMP |
| 47 | 65 | 30 | 1.1 | 0.9 | — | — | 3.0 | — | — | AMP |
| 48 | 60 | 30 | 3.4 | — | 1.6 | — | 5.0 | — | — | AMP |
| 49 | 55 | 30 | 5.4 | 4.6 | — | — | 5.0 | — | — | AMP |
| 50 | 94 | — | 0.55 | 0.45 | — | — | — | 5.0 | — | AMP |
| 51 | 91 | — | 0.55 | 0.45 | — | — | — | 8.0 | — | AMP |
| 52 | 79 | — | 0.55 | 0.45 | — | — | — | 20 | — | AMP |
| 53 | 75 | — | 3.4 | — | 1.6 | — | — | 20 | — | AMP |
| 54 | 70 | — | 5.4 | 4.6 | — | — | — | 20 | — | AMP |
| 55 | 55 | 36 | 0.55 | 0.45 | — | — | — | 8.0 | — | AMP |
| 56 | 50 | 25 | 3.4 | 1.6 | — | — | — | 20 | — | AMP |
| 57 | 96 | — | 0.3/0.9*) | 0.3 | — | — | 2.5 | — | — | NaOH |
| 58 | 93.5 | — | 0.3/0.9*) | 0.3 | — | — | 5.0 | — | — | NaOH |
| 59 | 85 | — | 2.5/5.0*) | 2.5 | — | — | 5.0 | — | — | NaOH |
| 60 | 80 | — | 5.0/5.0*) | 5.0 | — | — | 5.0 | — | — | NaOH |

TABLE 3-continued

| Ex. No. | VP [% by wt.] | MAM [% by wt.] | AMPS [% by wt.] | DMAPMAM [% by wt.] | VI [% by wt.] | NtBAEMA [% by wt.] | FAEMA [% by wt.] | Plex 6877-0 [% by wt.] | MBAA | Neutralized to pH 6-8 with |
|---|---|---|---|---|---|---|---|---|---|---|
| 61 | 80 | — | 6.5/5.0*) | — | 3.5 | — | 5.0 | — | — | NaOH |
| 62 | 70 | — | 6.5/15.0*) | — | 3.5 | — | 5.0 | — | — | NaOH |
| 63 | 88.5 | — | 0.3/0.9*) | 0.3 | — | — | — | 10 | — | NaOH |
| 64 | 78.5 | — | 0.3/0.9*) | 0.3 | — | — | — | 20 | — | NaOH |
| 65 | 70 | — | 2.5/5.0*) | 2.5 | — | — | — | 20 | — | NaOH |
| 66 | 65 | — | 5.0/5.0*) | 5.0 | — | — | — | 20 | — | NaOH |
| 67 | 95 | — | 0.4 | — | 0.3/3.3**) | — | 1.0 | — | — | AMP |
| 68 | 97.5 | — | 3.0 | — | 2.0/5.0**) | — | 2.5 | — | — | AMP |
| 69 | 70 | — | 6.5 | — | 3.5/15**) | — | 5.0 | — | — | AMP |
| 70 | 81 | — | 0.4 | — | 0.3/8.3**) | — | — | 10 | — | AMP |
| 71 | 60 | — | 1.0 | — | 0.6/18.4**) | — | — | 20 | — | AMP |
| 72 | 96.5 | — | 0.5 | 0.4 | 0.4 | — | 2.5 | — | 0.1 | AMP |
| 73 | 90 | — | 2.65 | 2.3 | 2.3 | — | 5.0 | — | 0.05 | AMP |
| 74 | 85 | — | 6.5 | — | — | — | 5.0 | — | 0.07 | AMP |
| 75 | 85 | — | 3.5/4.0*) | — | — | — | 5.0 | — | 0.07 | AMP |
| 76 | 89 | — | 0.5 | 0.4 | 0.4 | — | — | 10 | 0.1 | AMP |
| 77 | 75 | — | 2.65 | 2.3 | 2.3 | — | — | 20 | 0.05 | AMP |
| 78 | 70 | — | 3.0/3.93*) | 3.0 | 3.0 | — | — | 20 | 0.07 | AMP |
| 79 | 55 | 34 | 0.5 | 0.4 | 0.4 | — | — | 10 | 0.1 | AMP |
| 80 | 50 | 25 | 2.65 | 2.3 | 2.3 | — | — | 20 | 0.05 | AMP |

VP = vinylpyrrolidone
MAM = methylacrylamide
AMPS = 2-acrylamido-2-methylpropanesulfonic acid
*) = AMPS sodium salt
DMAPMAM = dimethylaminopropylmethacrylamide
VI = vinylimidazole
**) = VI quaternized with dimethyl sulfate
NtBAEMA = tert-Butylaminoethyl methacrylate
FAEMA = $C_{16}/C_{18}$-fatty alcohol ethoxylate methacrylate (25 EO)
Plex 6877-0 = Mixture of 25% by weight of $C_{16}/C_{18}$-fatty alcohol ethoxylate methacrylate (25 EO) and 75% by weight of methyl methacrylate (Rohm)
MBAA = Methylenebisacrylamide
AMP = 2-Amino-3-methylpropanol
***) firstly adjusted to a pH of >8 with NaOH, then adjusted to pH 6-8 by adding lactic acid Application Examples:

Use in Hair Cosmetics:

1. Conditioner shampoo (example Nos. 81-130)

|   |   | [%] |
|---|---|---|
| A) | Texapon NSO 28% strength (Sodium laureth sulphate/Henkel) | 50.0 |
|   | Comperlan KD (coamide DEA/Henkel) | 1.0 |
|   | Polymer 31-80 (20% aqueous solution) | 3.0 |
|   | Water | 17.0 |
|   | q.s. perfume oil | 27.5 |
| B) | Water | 27.5 |
|   | Sodium chloride | 1.5 |
|   | q.s. preservative ... |   |

Preparation: weigh in and dissolve and mix phases A and B separately with stirring, slowly stir phase B into phase A.

2. Setting foam: (examples 131-180)

|   | [%] |
|---|---|
| Polymer 31-80 (20% strength aqueous solution) | 5.0 |
| Cremophor A 25 (Ceteareth 25/BASF) | 0.2 |
| Comperlan KD (coamide DEA/Henkel) | 0.1 |
| Water | 84.7 |
| Dimethyl ether 3.5 bar (20° C.) | 10.0 |
| Further additive: perfume, preservative ... |   |

Preparation: weigh in and dissolve with stirring, bottle and add propellant gas.

3. Hair Gels with an Anionic Thickener: (Examples Nos. 181-230)

|   | [%] CTFA |
|---|---|
| Phase 1: |   |
| Polymer 31-80 (20% strength solution) | 15.0 |
| Glycerol | 0.3 |
| Water, dist. | 34.2 |
| 2-Amino-2-methylpropanol to pH 8 |   |
| Further additive: preservative, soluble ethoxylated silicone, perfume ... |   |
| Phase 2: |   |
| Aculyn 28 (1% strength aqueous suspension) | 50.0 |
| 2-Amino-2-methylpropanol | 0.5 |

Preparation: weigh in and homogenize. A clear solid gel forms in phase 2. Slowly stir phase 1 into phase 2.

4. Hair gels with a further setting polymer and thickener: (examples Nos. 231-280)

|   | [%] CTFA |
|---|---|
| Phase 1: |   |
| Polymer 31-80 (20% strength aqueous solution) | 7.0 |

-continued

| | [%] | CTFA |
|---|---|---|
| Luviset Clear ® | 1.0 | VP/Methacry-lamide/Vinyl-imidazole copolymer |
| Belsil DMC 6031 | 0.1 | ethoxylated polysiloxane (Goldschmidt) |
| Uvinul MS 40 | 0.2 | Benzophenone-4 |
| Glycerol | 0.1 | |
| D-Panthenol USP | 0.3 | Panthenol |
| Ethanol | 10.0 | |
| Water, dist. | 31.0 | |
| Further additive: preservative, soluble ethoxylated silicone, perfume . . . | | |
| Phase 2: | | |
| Acuyln 28 (1% strength aqueous suspension) | 30.0 | |
| 2-Amino-2-methylpropanol | 0.3 | |
| Water, dist. | 20.0 | |

Preparation: weigh in and homogenize. Slowly stir phase 1 into phase 2. A clear solid gel forms in phase 2.

5. Anionic Self-Thickening Hair Gels
(Example Nos. 281-330) (Without Additional Thickener):

| | [%] | CTFA |
|---|---|---|
| Polymer 31-80 (20% strength aqueous solution) | 10.0 | |
| Luviset Clear ® | 2.0 | VP/Methacry-lamide/Vinyl-imidazole copolymer |
| Uvinul MS 40 | 0.2 | Benzophenone-4 |
| D-Panthenol USP | 0.3 | Panthenol |
| Water, dist. | 57.5 | |
| Further additive: preservative, soluble ethoxylated silicone, perfume . . . | | |

Preparation: weigh in and homogenize. The polymer solution is then adjusted to pH 7.5 with 2-amino-2-methylpropanol (25% strength). A viscous clear gel is formed.

Use in Skin Cosmetics:
6. Standard O/W Cream: (Examples Nos. 331-380)

| | % | CTFA name |
|---|---|---|
| Oil phase | | |
| Cremophor A6 | 3.0 | Ceteareth-6- (and) Stearyl alcohol Ceteareth-25 |
| Cremophor A25 | 3.0 | Glyceryl Stearate |
| Glycerol monostearate s.e. | 2.5 | |
| Paraffin oil | | Paraffin oil |
| Cetyl alcohol | 7.5 | Cetyl alcohol |
| Luvitol EHO | 3.5 | Cetearyl octanoate |
| Vitamin E acetate | 3.2 | Tocopherol acetate |
| Nip-Nip | 1.0 | Methyl and propyl-4-hydroxy-benzide (7:3) |
| | 0.1 | |
| Water phase: | | |
| Polymer 31-80 (20% strength aqueous solution) | 3.0 | |
| Water | 74.6 | Water |
| 1,2-Propylene glycol | 1.5 | Propylene Glycol |
| Germall II | 0.1 | Imidazolidinylurea |

Preparation: Weigh in and homogenize the oil phase and water phase separately with stirring at a temperature of about 80° C. Slowly stir the water phase into the oil phase. Slowly cool to room temperature with stirring.

We claim:

1. An ampholytic copolymer obtained by free-radical copolymerization of
   a) at least one compound with a free-radically polymerizable, $\alpha,\beta$-ethylenically unsaturated double bond and at least one anionogenic and/or anionic group per molecule selected from the group consisting of acrylic acid, methacrylic acid and 2-acrylamido-2-methylpropanesulfonic acid,
   b) at least one compound with a free-radically polymerizable, $\alpha,\beta$-ethylenically unsaturated double bond and at least one cationogenic and/or cationic group per molecule selected from the group consisting of vinylimidazole, tert.-butylaminoethyl methacrylate and mixtures thereof, and,
   c) at least one $\alpha,\beta$-ethylenically unsaturated amide-group-containing compound selected from the group consisting of acrylamide, methacrylamide, N- vinylpyrrolidone, N-vinylcaprolactam, N-vinylformamide, N-vinylacetamide and mixtures thereof,
   where the quantitative molar ratio of compounds a) to compounds b) is from 0.5:1 to less than 2:1.

2. A polyelectrolyte complex comprising at least one ampholytic copolymer, as defined in claim 1, and at least one further polyelectrolyte different therefrom.

3. The ampholytic copolymer as claimed in claim 1, where the quantitative molar ratio of compounds a) to compounds b) is in a range from 0.7:1 to 1.8:1.

4. The composition as claimed in claim 1, where at least some of the compounds a) and b) are used in the form of a monomer composition, where the molar ratio of anionogenic groups of component a) to cationogenic groups of component b) is about 1:1.

5. The composition as claimed in claim 1, which additionally comprises, in copolymerized form, at least one further monomer d) selected from the group consisting of esters of $\alpha,\beta$-ethylenically unsaturated mono- and dicarboxylic acids with $C_1$-$C_{30}$-alkanols and $C_1$-$C_{30}$-alkanediols, amides of $\alpha,\beta$- ethylenically unsaturated mono- and dicarboxylic acids with $C_2$-$C_{30}$-aminoalcohols which have a primary or secondary amino group, N-alkyl- and N,N-dialkylamides of $\alpha,\beta$-ethylenically unsaturated monocarboxylic acids which, in addition to the carbonyl carbon atom of the amide group, have more than 8 further carbon atoms, esters of vinyl alcohol and allyl alcohol with $C_1$-$C_{30}$-monocarboxylic acids, vinyl ethers, vinylaromatics, vinyl halides, vinylidene halides, $C_1$-$C_8$-monoolefins, nonaromatic hydrocarbons with at least two conjugated double bonds, siloxane macromers and mixtures thereof.

6. The composition as claimed in claim 1, which additionally comprises, as component e), at least one polyether acrylate in copolymerized form.

7. The composition as claimed in claim 1, which is obtainable by free-radical copolymerization in the presence of a component g) which is selected from the group consisting of
   g1) polyether-containing compounds,
   g2) polymers which have at least 50% by weight of repeat units which are derived from vinyl alcohol,
   g3) cellulose, starch and derivatives thereof, and mixtures thereof.

8. The composition as claimed in claim 1, which additionally comprises, in copolymerized form, at least one free-radically polymerizable crosslinking compound f) with at least two $\alpha,\beta$-ethylenically unsaturated double bonds per molecule.

* * * * *